United States Patent
Foerster et al.

(10) Patent No.: US 7,682,374 B2
(45) Date of Patent: Mar. 23, 2010

(54) KNOTLESS SUTURE LOCK AND BONE ANCHOR IMPLANT METHOD

(75) Inventors: Seth Foerster, San Clemente, CA (US); Norman Gordon, Irvine, CA (US); Francis Vijay, Irvine, CA (US); Minh Tran, Littleton, CO (US)

(73) Assignee: ArthroCare Corporation, Austin, TX (US)

( * ) Notice: Subject to any disclaimer, the term of this patent is extended or adjusted under 35 U.S.C. 154(b) by 910 days.

(21) Appl. No.: 11/375,691

(22) Filed: Mar. 13, 2006

(65) Prior Publication Data

US 2006/0293710 A1 Dec. 28, 2006

Related U.S. Application Data

(63) Continuation-in-part of application No. 10/690,438, filed on Oct. 21, 2003, now abandoned.

(51) Int. Cl.
*A61B 17/04* (2006.01)
(52) U.S. Cl. .............................. 606/232; 606/148
(58) Field of Classification Search ................ 606/232, 606/60, 139, 228, 74, 75, 233, 148
See application file for complete search history.

(56) References Cited

U.S. PATENT DOCUMENTS

| 918,570 | A | 4/1909 | Mather ................ 292/318 |
|---|---|---|---|
| 1,153,053 | A | 9/1915 | Forster ................ 43/44.85 |
| 1,565,041 | A | 12/1925 | Arneu ................ 24/129 R |
| 2,269,963 | A | 1/1942 | Wrapler ................ 604/604 |
| 2,485,531 | A | 10/1949 | Dzus et al. ................ 128/92 |
| 2,600,395 | A | 6/1952 | Domoj et al. ................ 87/13 |
| 3,143,916 | A | 8/1964 | Rice ................ 85/71 |
| 3,942,407 | A | 3/1976 | Mortensen ................ 85/71 |

(Continued)

FOREIGN PATENT DOCUMENTS

DE  3509417  9/1986

(Continued)

OTHER PUBLICATIONS

PCT Search Report and Written Opinion for PCT/US06/20657 7 pgs.

(Continued)

*Primary Examiner*—Pedro Philogene
(74) *Attorney, Agent, or Firm*—Matthew Scheele; Brian E. Szymczak

(57) ABSTRACT

A knotless suture lock and bone anchor wherein a suture, looped through a tissue, is threaded through a plurality of body holes in the anchor to cinch the suture and tissue to the anchor without tying a suture knot on the tissue, and wherein the anchor is adapted for embedding in a bone. The tissue is secured to the anchor by suturing the tissue without a suture knot, fastening the standing leg portion of the suture on a suture leg-anchoring structure, and threading the working leg portion of the suture through the body holes. Pulling on the working leg portion of the suture tightens the suture on the body structure and cinches the loop without a suture knot on the tissue. The bone-embedding structure comprises a plurality of barbs adapted to resist pullout of the anchor from the bone.

19 Claims, 25 Drawing Sheets

U.S. PATENT DOCUMENTS

| | | | |
|---|---|---|---|
| 3,946,740 A | 3/1976 | Bassett | 128/334 |
| 3,994,521 A | 11/1976 | Van Gompel | 292/319 |
| 4,109,658 A | 8/1978 | Hughes | 128/340 |
| 4,210,148 A | 7/1980 | Stivala | 606/232 |
| 4,274,324 A | 6/1981 | Giannuzzi | 411/38 |
| 4,301,551 A | 11/1981 | Dore et al. | 623/13.3 |
| 4,319,428 A | 3/1982 | Fox | 47/42 |
| 4,345,601 A | 8/1982 | Fukuda | 128/339 |
| 4,373,530 A | 2/1983 | Kilejian | 128/334 R |
| 4,384,389 A | 5/1983 | Sato | 24/136 K |
| 4,409,974 A | 10/1983 | Freedland | 128/92 |
| 4,456,270 A | 6/1984 | Zettl et al. | 279/62 |
| 4,467,478 A | 8/1984 | Jurgutis | 606/75 |
| 4,483,023 A | 11/1984 | Hoffman, Jr. et al. | 623/13.15 |
| 4,493,323 A | 1/1985 | Albright et al. | 128/340 |
| 4,590,928 A | 5/1986 | Hunt et al. | 606/72 |
| 4,597,776 A | 7/1986 | Ullman et al. | 48/197 R |
| 4,605,414 A | 8/1986 | Czajka | 623/13.11 |
| 4,621,640 A | 11/1986 | Mulhollan et al. | 128/340 |
| 4,635,637 A | 1/1987 | Schreiber | 128/337 |
| 4,657,461 A | 4/1987 | Smith | 411/340 |
| 4,672,957 A | 6/1987 | Hourahane | 606/80 |
| 4,712,542 A | 12/1987 | Daniel et al. | 606/96 |
| 4,721,103 A | 1/1988 | Freedland | 128/92 |
| 4,731,084 A | 3/1988 | Dunn et al. | 623/13.19 |
| 4,738,255 A | 4/1988 | Goble et al. | 128/92 YF |
| 4,741,330 A | 5/1988 | Hayhurst | 123/43 R |
| 4,750,492 A | 6/1988 | Jacobs | 606/230 |
| 4,772,286 A | 9/1988 | Goble et al. | 623/13.14 |
| 4,779,616 A | 10/1988 | Johnson et al. | 606/148 |
| 4,809,408 A | 3/1989 | Abrahamson | 24/136 K |
| 4,823,780 A | 4/1989 | Odensten et al. | 606/96 |
| 4,828,439 A | 5/1989 | Giannuzzi | 411/37 |
| 4,851,005 A | 7/1989 | Hunt et al. | 623/18 |
| 4,870,957 A | 10/1989 | Goble et al. | 606/73 |
| 4,917,700 A | 4/1990 | Aikins | 623/13.19 |
| 4,926,860 A | 5/1990 | Stice et al. | 606/144 |
| 4,935,027 A | 6/1990 | Yoon | 606/146 |
| 4,946,467 A | 8/1990 | Ohi et al. | 606/228 |
| 4,946,468 A | 8/1990 | Li | 606/232 |
| 4,957,498 A | 9/1990 | Caspari | 606/146 |
| 4,968,315 A | 11/1990 | Gatturna | 606/72 |
| 4,981,149 A | 1/1991 | Yoon et al. | 128/898 |
| 4,987,665 A | 1/1991 | Dumican | 28/218 |
| 5,002,550 A | 3/1991 | Li | 606/139 |
| 5,019,093 A | 5/1991 | Kaplan et al. | 606/228 |
| 5,037,422 A | 8/1991 | Hayhurst | 606/72 |
| 5,046,513 A | 9/1991 | Gatturna | 128/898 |
| 5,059,201 A | 10/1991 | Asnis | 606/144 |
| 5,062,344 A | 11/1991 | Gerker | 87/8 |
| 5,085,661 A | 2/1992 | Moss | 606/139 |
| 5,147,166 A | 9/1992 | Harker | 411/29 |
| 5,195,542 A | 3/1993 | Gazielly et al. | 60/244 |
| 5,203,787 A | 4/1993 | Noblitt et al. | 606/232 |
| RE34,293 E | 6/1993 | Goble et al. | 623/13.14 |
| 5,217,495 A | 6/1993 | Kaplan et al. | 623/13.18 |
| 5,219,359 A | 6/1993 | McQuilkin et al. | 606/232 |
| 5,224,946 A | 7/1993 | Hayhurst | 606/72 |
| 5,258,016 A | 11/1993 | DiPoto et al. | 606/232 |
| 5,263,984 A | 11/1993 | Li | 623/13.18 |
| 5,275,176 A | 1/1994 | Chandler | 606/242 |
| 5,304,184 A | 4/1994 | Hathaway et al. | 606/144 |
| 5,324,308 A | 6/1994 | Pierce | 606/232 |
| 5,326,205 A | 7/1994 | Anspach, Jr. et al. | 411/43 |
| 5,330,442 A | 7/1994 | Green | 606/232 |
| 5,330,468 A | 7/1994 | Burkhart | 606/96 |
| 5,330,488 A | 7/1994 | Goldrath | 606/148 |
| 5,336,240 A | 8/1994 | Metzler | 606/232 |
| 5,354,298 A * | 10/1994 | Lee et al. | 606/139 |
| 5,364,407 A | 11/1994 | Poll | 606/139 |
| 5,376,118 A | 12/1994 | Kaplan et al. | 623/23.72 |
| 5,383,905 A | 1/1995 | Gold et al. | 606/232 |
| 5,405,352 A | 4/1995 | Weston | 606/148 |
| 5,405,359 A | 4/1995 | Pierce | 606/232 |
| 5,413,579 A | 5/1995 | Du | 606/87 |
| 5,417,691 A | 5/1995 | Hayhurst | 606/72 |
| 5,417,699 A | 5/1995 | Klein et al. | 606/139 |
| 5,417,712 A | 5/1995 | Whitaker et al. | 606/232 |
| 5,431,666 A | 7/1995 | Sauer et al. | 606/139 |
| 5,441,508 A | 8/1995 | Gazielly et al. | 606/151 |
| 5,445,167 A | 8/1995 | Yoon et al. | 128/898 |
| 5,450,860 A | 9/1995 | O'Connor | 606/224 |
| 5,454,823 A | 10/1995 | Richardson et al. | 606/148 |
| 5,464,427 A | 11/1995 | Curtis et al. | 606/232 |
| 5,470,335 A | 11/1995 | Du Toit | 606/73 |
| 5,472,452 A | 12/1995 | Trott | 606/232 |
| 5,480,403 A | 1/1996 | Lee et al. | 606/72 |
| 5,486,197 A | 1/1996 | Le et al. | 606/232 |
| 5,499,991 A | 3/1996 | Garman et al. | 606/148 |
| 5,501,683 A | 3/1996 | Trott | 606/72 |
| 5,501,695 A | 3/1996 | Anspach, Jr. et al. | 606/72 |
| 5,505,735 A | 4/1996 | Li | 606/72 |
| 5,514,159 A | 5/1996 | Matula et al. | 606/232 |
| 5,522,820 A | 6/1996 | Caspari et al. | 606/148 |
| 5,527,322 A | 6/1996 | Klein et al. | 606/144 |
| 5,527,343 A | 6/1996 | Bonutti | 606/232 |
| 5,531,763 A | 7/1996 | Mastri et al. | 606/148 |
| 5,531,792 A | 7/1996 | Huene | 623/16 |
| 5,534,012 A | 7/1996 | Bonutti | 606/232 |
| 5,540,703 A | 7/1996 | Barker, Jr. et al. | 606/139 |
| 5,545,180 A | 8/1996 | Le et al. | 606/232 |
| 5,549,617 A | 8/1996 | Green et al. | 606/144 |
| 5,549,630 A | 8/1996 | Bonutti | 606/232 |
| 5,553,360 A | 9/1996 | Lucas et al. | 24/136 K |
| 5,562,689 A | 10/1996 | Green et al. | 606/151 |
| 5,569,305 A | 10/1996 | Bonutti | 606/232 |
| 5,569,306 A | 10/1996 | Thal | 606/232 |
| 5,571,104 A | 11/1996 | Li | 606/72 |
| 5,571,120 A | 11/1996 | Yoon | 606/148 |
| 5,573,540 A | 11/1996 | Yoon | 606/139 |
| 5,573,542 A | 11/1996 | Stevens | 606/144 |
| 5,573,548 A | 11/1996 | Nazre et al. | 606/232 |
| 5,575,801 A | 11/1996 | Habermeyer et al. | 606/148 |
| 5,584,835 A | 12/1996 | Greenfield | 606/73 |
| 5,584,839 A | 12/1996 | Gieringer | 606/96 |
| 5,584,860 A | 12/1996 | Goble et al. | 606/232 |
| 5,584,862 A | 12/1996 | Bonutti | 606/232 |
| 5,591,207 A | 1/1997 | Coleman | 606/232 |
| 5,593,189 A | 1/1997 | Little | 289/17 |
| 5,601,558 A | 2/1997 | Torrie et al. | 606/72 |
| 5,609,597 A | 3/1997 | Lehrer | 606/139 |
| 5,611,801 A | 3/1997 | Songer | 606/73 |
| 5,613,974 A | 3/1997 | Andreas et al. | 606/144 |
| 5,618,290 A | 4/1997 | Toy et al. | 606/139 |
| 5,618,314 A | 4/1997 | Harwin et al. | 606/232 |
| 5,626,614 A | 5/1997 | Hart | 606/232 |
| 5,630,824 A | 5/1997 | Hart | 606/139 |
| 5,632,748 A | 5/1997 | Beck, Jr. et al. | 606/72 |
| 5,645,589 A | 7/1997 | Li | 623/16 |
| 5,647,874 A | 7/1997 | Hayhurst | 606/72 |
| 5,649,940 A | 7/1997 | Hart et al. | 606/148 |
| 5,658,313 A | 8/1997 | Thal | 606/232 |
| 5,665,110 A | 9/1997 | Chervitz et al. | 606/232 |
| 5,665,112 A | 9/1997 | Thal | 606/232 |
| 5,667,528 A | 9/1997 | Colligan | 606/224 |
| D385,352 S | 10/1997 | Bales et al. | D24/145 |
| 5,681,333 A | 10/1997 | Burkhart et al. | 606/148 |
| 5,681,351 A | 10/1997 | Jamiolkowski | 606/232 |
| 5,683,418 A | 11/1997 | Luscombe et al. | 606/232 |
| 5,683,419 A | 11/1997 | Thal | 606/232 |
| 5,690,649 A | 11/1997 | Li | 606/139 |
| 5,693,060 A * | 12/1997 | Martin | 606/148 |
| 5,697,950 A | 12/1997 | Fucci et al. | 606/232 |
| 5,702,397 A | 12/1997 | Goble et al. | 606/72 |

| Patent | Date | Inventor | Class |
|---|---|---|---|
| 5,702,398 A | 12/1997 | Tarabishy | 606/72 |
| 5,707,362 A | 1/1998 | Yoon | 604/164 |
| 5,707,394 A | 1/1998 | Miller et al. | 606/232 |
| 5,709,708 A | 1/1998 | Thal | 606/232 |
| 5,720,765 A | 2/1998 | Thal | 606/232 |
| 5,725,541 A | 3/1998 | Anspach, III et al. | 606/151 |
| 5,728,136 A | 3/1998 | Thal | 606/232 |
| 5,733,307 A * | 3/1998 | Dinsdale | 606/232 |
| 5,741,281 A | 4/1998 | Martin | 606/148 |
| 5,741,282 A | 4/1998 | Anspach, III et al. | 606/151 |
| 5,766,250 A | 6/1998 | Chervitz et al. | 623/13 |
| 5,782,863 A | 7/1998 | Bartlett | 606/232 |
| 5,782,864 A | 7/1998 | Lizardi | 606/232 |
| 5,782,865 A | 7/1998 | Grotz | 606/72 |
| 5,791,899 A | 8/1998 | Sachdeva | 433/173 |
| 5,792,152 A | 8/1998 | Klein et al. | 606/144 |
| 5,797,927 A | 8/1998 | Yoon | 606/144 |
| 5,797,963 A | 8/1998 | McDevitt | 606/232 |
| 5,810,848 A | 9/1998 | Hayhurst | 606/144 |
| 5,810,854 A | 9/1998 | Beach | 606/232 |
| 5,814,052 A | 9/1998 | Nakao et al. | 606/148 |
| 5,814,071 A | 9/1998 | McDevitt et al. | 606/232 |
| 5,814,072 A | 9/1998 | Bonutti | 606/232 |
| 5,843,111 A | 12/1998 | Vijfvinkel | 606/171 |
| 5,849,004 A | 12/1998 | Bramlet | 606/232 |
| 5,860,978 A | 1/1999 | McDevitt | 606/72 |
| 5,860,991 A | 1/1999 | Klein et al. | 606/144 |
| 5,860,992 A | 1/1999 | Daniel et al. | 606/145 |
| 5,868,789 A | 2/1999 | Heubner | 606/232 |
| 5,879,372 A | 3/1999 | Bartlett | 606/232 |
| 5,882,340 A | 3/1999 | Yoon | 604/164 |
| 5,885,294 A | 3/1999 | Pedlick et al. | 606/80 |
| 5,891,168 A | 4/1999 | Thal | 606/232 |
| 5,893,850 A | 4/1999 | Cachia | 606/72 |
| 5,902,311 A | 5/1999 | Andreas et al. | 606/144 |
| 5,904,692 A | 5/1999 | Steckel et al. | 606/139 |
| 5,911,721 A | 6/1999 | Nicholson et al. | 606/72 |
| 5,921,994 A | 7/1999 | Andreas et al. | 606/144 |
| 5,935,129 A | 8/1999 | Mdevitt | 606/72 |
| 5,941,900 A | 8/1999 | Bonutti | 606/232 |
| 5,941,901 A | 8/1999 | Egan | 606/232 |
| 5,944,724 A | 8/1999 | Lizardi | 606/104 |
| 5,944,739 A | 8/1999 | Zlock et al. | 606/232 |
| 5,947,982 A | 9/1999 | Duran | 606/139 |
| 5,948,000 A | 9/1999 | Larsen et al. | 606/232 |
| 5,948,001 A | 9/1999 | Larsen | 606/232 |
| 5,948,002 A | 9/1999 | Bonutti | 606/232 |
| 5,957,953 A | 9/1999 | DiPoto et al. | 606/232 |
| 5,957,968 A | 9/1999 | Belden et al. | 607/126 |
| 5,961,530 A | 10/1999 | Moore et al. | 606/148 |
| 5,961,538 A | 10/1999 | Pedlick et al. | 606/232 |
| 5,968,044 A | 10/1999 | Nicholson et al. | 606/72 |
| 5,980,558 A | 11/1999 | Wiley | 606/232 |
| 5,980,559 A | 11/1999 | Bonutti | 606/232 |
| 5,984,933 A | 11/1999 | Yoon | 606/148 |
| 5,993,459 A | 11/1999 | Larsen | 606/104 |
| 6,001,104 A | 12/1999 | Benderev et al. | 606/80 |
| 6,001,109 A | 12/1999 | Kontos | 606/148 |
| 6,007,566 A | 12/1999 | Wenstrom | 606/232 |
| 6,007,567 A | 12/1999 | Bonutti | 606/232 |
| 6,010,525 A | 1/2000 | Bonutti et al. | 606/232 |
| 6,013,083 A | 1/2000 | Bennett | 606/104 |
| 6,017,346 A | 1/2000 | Grotz | 606/72 |
| 6,022,360 A | 2/2000 | Reimels et al. | 606/144 |
| 6,022,373 A | 2/2000 | Li | 606/232 |
| 6,024,758 A | 2/2000 | Thal | 606/232 |
| 6,033,430 A | 3/2000 | Bonutti | 606/232 |
| 6,036,699 A | 3/2000 | Andreas et al. | 606/139 |
| 6,045,571 A | 4/2000 | Hill et al. | 606/228 |
| 6,045,572 A | 4/2000 | Johnson et al. | 606/232 |
| 6,045,573 A | 4/2000 | Wenstrom et al. | 606/232 |
| 6,045,574 A | 4/2000 | Thal | 606/232 |
| 6,048,351 A | 4/2000 | Gordon et al. | 606/144 |
| 6,051,006 A | 4/2000 | Shluzas et al. | 606/148 |
| 6,053,935 A | 4/2000 | Brenneman et al. | 606/232 |
| 6,056,773 A | 5/2000 | Bonutti | 606/232 |
| 6,068,648 A | 5/2000 | Cole et al. | 606/232 |
| 6,086,608 A | 7/2000 | Elk et al. | 606/232 |
| 6,096,051 A | 8/2000 | Kortenbach et al. | 606/144 |
| 6,102,934 A | 8/2000 | Li | 606/232 |
| 6,117,160 A | 9/2000 | Bonutti | 606/215 |
| 6,117,161 A | 9/2000 | Li | 606/232 |
| 6,143,004 A | 11/2000 | Davis et al. | 606/144 |
| 6,146,386 A | 11/2000 | Blackman | 606/103 |
| 6,146,406 A | 11/2000 | Shluzas et al. | 606/232 |
| 6,149,669 A | 11/2000 | Li | 606/232 |
| 6,156,039 A | 12/2000 | Thal | 606/72 |
| 6,156,056 A | 12/2000 | Kearns et al. | 606/232 |
| 6,159,235 A | 12/2000 | Kim | 606/232 |
| 6,162,537 A | 12/2000 | Martin et al. | 428/373 |
| 6,171,317 B1 | 1/2001 | Jackson et al. | 606/148 |
| 6,200,329 B1 | 3/2001 | Fung et al. | 606/232 |
| 6,200,893 B1 | 3/2001 | Sneh | 438/685 |
| 6,206,895 B1 | 3/2001 | Levison | 606/144 |
| 6,217,592 B1 | 4/2001 | Freda et al. | 606/145 |
| 6,221,107 B1 | 4/2001 | Steiner et al. | 623/13.14 |
| 6,228,096 B1 | 5/2001 | Marchand | 606/139 |
| 6,241,736 B1 | 6/2001 | Sater | 606/104 |
| 6,267,766 B1 | 7/2001 | Burkhart | 606/72 |
| 6,280,474 B1 | 8/2001 | Cassidy et al. | 623/16.11 |
| 6,293,961 B2 | 9/2001 | Schwartz | 606/232 |
| 6,315,781 B1 | 11/2001 | Reinhardt | 606/108 |
| 6,319,252 B1 | 11/2001 | McDevitt et al. | 606/60 |
| 6,319,269 B1 | 11/2001 | Li | 606/232 |
| 6,319,271 B1 | 11/2001 | Schwartz | 606/232 |
| 6,328,758 B1 | 12/2001 | Tornier et al. | 606/232 |
| 6,355,053 B1 | 3/2002 | Li | 606/232 |
| 6,409,743 B1 | 6/2002 | Fenton | 606/232 |
| 6,451,030 B2 | 9/2002 | Li et al. | 606/139 |
| 6,464,713 B2 | 10/2002 | Bonutti | 606/232 |
| 6,471,715 B1 | 10/2002 | Weiss | 606/216 |
| 6,475,230 B1 | 11/2002 | Bonutti et al. | 606/232 |
| 6,491,714 B1 | 12/2002 | Bennett | 606/232 |
| 6,517,542 B1 * | 2/2003 | Papay et al. | 606/232 |
| 6,520,980 B1 | 2/2003 | Foerster | 606/232 |
| 6,524,317 B1 | 2/2003 | Ritchart et al. | 606/72 |
| 6,527,794 B1 | 3/2003 | McDevitt et al. | 606/232 |
| 6,540,770 B1 | 4/2003 | Tornier et al. | 606/232 |
| 6,569,187 B1 | 5/2003 | Bonutti et al. | 606/232 |
| 6,575,987 B2 | 6/2003 | Gellman et al. | 606/151 |
| 6,582,453 B1 | 6/2003 | Tran et al. | 606/232 |
| 6,585,730 B1 | 7/2003 | Foerster | 606/232 |
| 6,635,073 B2 | 10/2003 | Bonutti | 606/232 |
| 6,638,279 B2 | 10/2003 | Bonutti | 606/60 |
| 6,645,227 B2 | 11/2003 | Fallin et al. | 606/232 |
| 6,648,903 B1 | 11/2003 | Pierson, III | 606/232 |
| 6,652,561 B1 | 11/2003 | Tran | 606/232 |
| 6,656,183 B2 | 12/2003 | Colleran et al. | 606/232 |
| 6,660,008 B1 | 12/2003 | Foerster et al. | 606/72 |
| 6,660,023 B2 | 12/2003 | McDevitt et al. | 606/232 |
| 6,679,896 B2 | 1/2004 | Gellman et al. | 606/148 |
| 6,682,549 B2 | 1/2004 | Bartlett | 606/232 |
| 6,689,154 B2 | 2/2004 | Bartlett | 606/232 |
| 6,692,516 B2 | 2/2004 | West et al. | 606/232 |
| 6,736,829 B1 | 5/2004 | Li et al. | 606/232 |
| 6,770,076 B2 | 8/2004 | Foerster | 606/72 |
| 6,780,198 B1 | 8/2004 | Gregoire et al. | 606/232 |
| 6,855,157 B2 | 2/2005 | Foerster et al. | 606/232 |
| 6,860,887 B1 | 3/2005 | Frankle | 606/104 |
| 6,972,027 B2 | 12/2005 | Fallin et al. | 606/232 |
| 7,083,638 B2 | 8/2006 | Foerster | 606/232 |
| 7,090,690 B2 | 8/2006 | Foerster et al. | 606/232 |
| 7,104,999 B2 | 9/2006 | Overaker | 606/142 |
| 7,150,757 B2 * | 12/2006 | Fallin et al. | 606/232 |
| 7,247,164 B1 | 7/2007 | Ritchart et al. | 606/232 |
| 7,329,272 B2 | 2/2008 | Burkhart et al. | 606/232 |

| | | | |
|---|---|---|---|
| 2003/0167062 A1 | 9/2003 | Gambale | 606/232 |
| 2003/0191498 A1 | 10/2003 | Foerster et al. | 606/232 |
| 2003/0195563 A1 | 10/2003 | Foerster | 606/232 |
| 2003/0195564 A1 | 10/2003 | Tran et al. | 606/232 |
| 2004/0138706 A1 | 7/2004 | Abrams et al. | 606/232 |
| 2004/0236336 A1 | 11/2004 | Foerster et al. | 606/72 |
| 2004/0243179 A1 | 12/2004 | Foerster | 606/232 |
| 2004/0260345 A1 | 12/2004 | Foerster | 606/232 |
| 2005/0080455 A1 | 4/2005 | Schmieding et al. | 606/232 |
| 2005/0240226 A1 | 10/2005 | Foerster et al. | 606/232 |
| 2005/0277986 A1 | 12/2005 | Foerster | 606/232 |
| 2006/0004364 A1 | 1/2006 | Green et al. | 606/72 |
| 2006/0079904 A1 | 4/2006 | Thal | 606/72 |
| 2006/0271060 A1 | 11/2006 | Gordon | 606/232 |
| 2006/0271105 A1 | 11/2006 | Foerster | 606/232 |
| 2006/0293710 A1 | 12/2006 | Foerster | 606/72 |
| 2007/0142838 A1 | 6/2007 | Jordan | 606/75 |
| 2007/0203508 A1 | 8/2007 | White et al. | 606/148 |
| 2008/0015594 A1 | 1/2008 | Ritchart et al. | 606/72 |
| 2008/0051836 A1 | 2/2008 | Foerster et al. | 606/232 |
| 2008/0319478 A1 | 12/2008 | Foerster et al. | 606/148 |
| 2009/0069823 A1 | 3/2009 | Foerster et al. | 606/103 |

FOREIGN PATENT DOCUMENTS

| | | |
|---|---|---|
| EP | 0 535 906 A2 | 4/1993 |
| EP | 0 571 686 A1 | 12/1993 |
| EP | 0 611 557 A2 | 8/1994 |
| EP | 1 072 234 A2 | 1/2001 |
| EP | 1 072 237 A1 | 1/2001 |
| FR | 2777442 | 10/1999 |
| FR | 2777477 | 10/1999 |
| JP | 2286468 | 11/1990 |
| JP | 8-52154 | 2/1996 |
| WO | 89/10096 | 11/1989 |
| WO | 91/06247 | 5/1991 |
| WO | 95/06439 | 3/1995 |
| WO | 95/25469 | 9/1995 |
| WO | 99/53843 | 10/1999 |
| WO | 99/53844 | 10/1999 |
| WO | 02/21997 | 3/2002 |
| WO | 03/049620 | 6/2003 |

OTHER PUBLICATIONS

PCT Search Report and Written Opinion for PCT/US06/21125 6pgs.
PCT International Search Report for PCT/US01/21905 3pgs.
PCT International Preliminary Examination Report for PCT/US01/21905 3pgs.
PCT International Search Report for PCT/US01/17689 3pgs.
PCT International Preliminary Examination Report for PCT/US01/17689 15pgs.
PCT International Search Report for PCT/US02/17493 1pg.
PCT International Preliminary Examination Report for PCT/US02/17493 4pgs.
PCT International Search Report for PCT/US02/41018 2pgs.
PCT International Preliminary Examination Report for PCT/US02/41018 3pgs.
PCT International Search Report for PCT/US02/04231 1pg.
PCT International Preliminary Examination Report for PCT/US02/04231 3pgs.
PCT International Search Report for PCT/US03/35695 1pg.
PCT International Preliminary Examination Report for PCT/US03/35695 4pgs.
EP Partial European Search Report for EP02742470 3pgs.
EP Supplementary European Search Report for EP02742470 5pgs.
UK Search Report for GB 0816111.9 3pgs.
European Search Report for EP 02734649 3pgs.

* cited by examiner

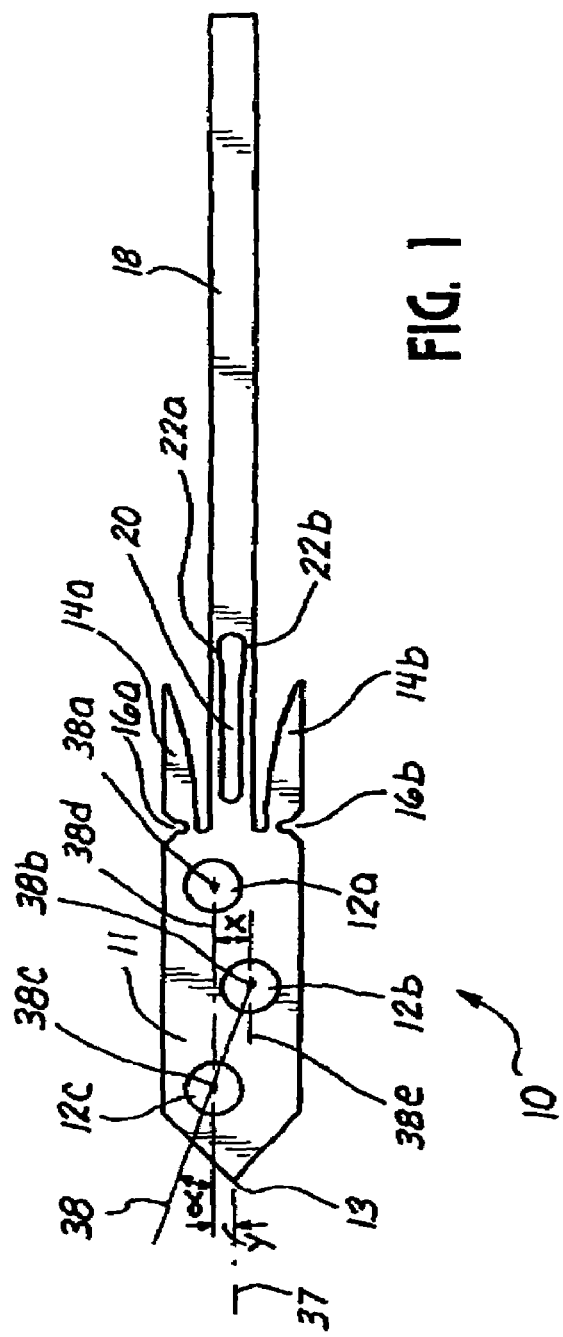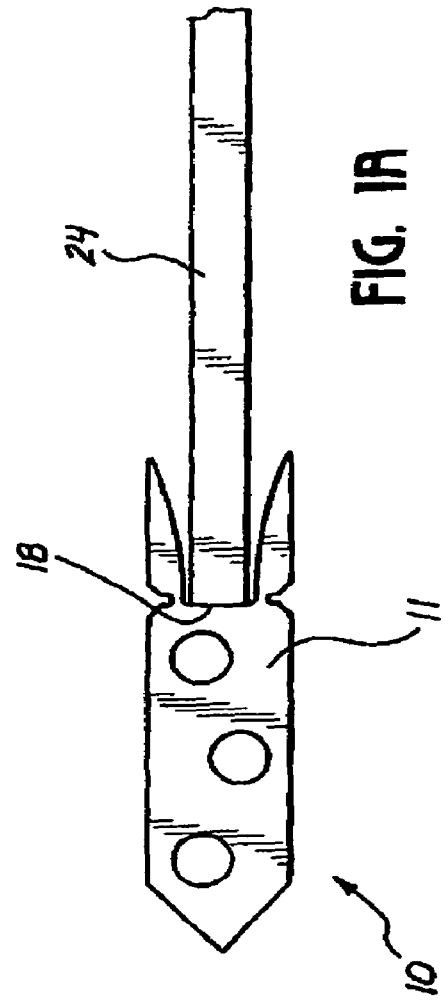

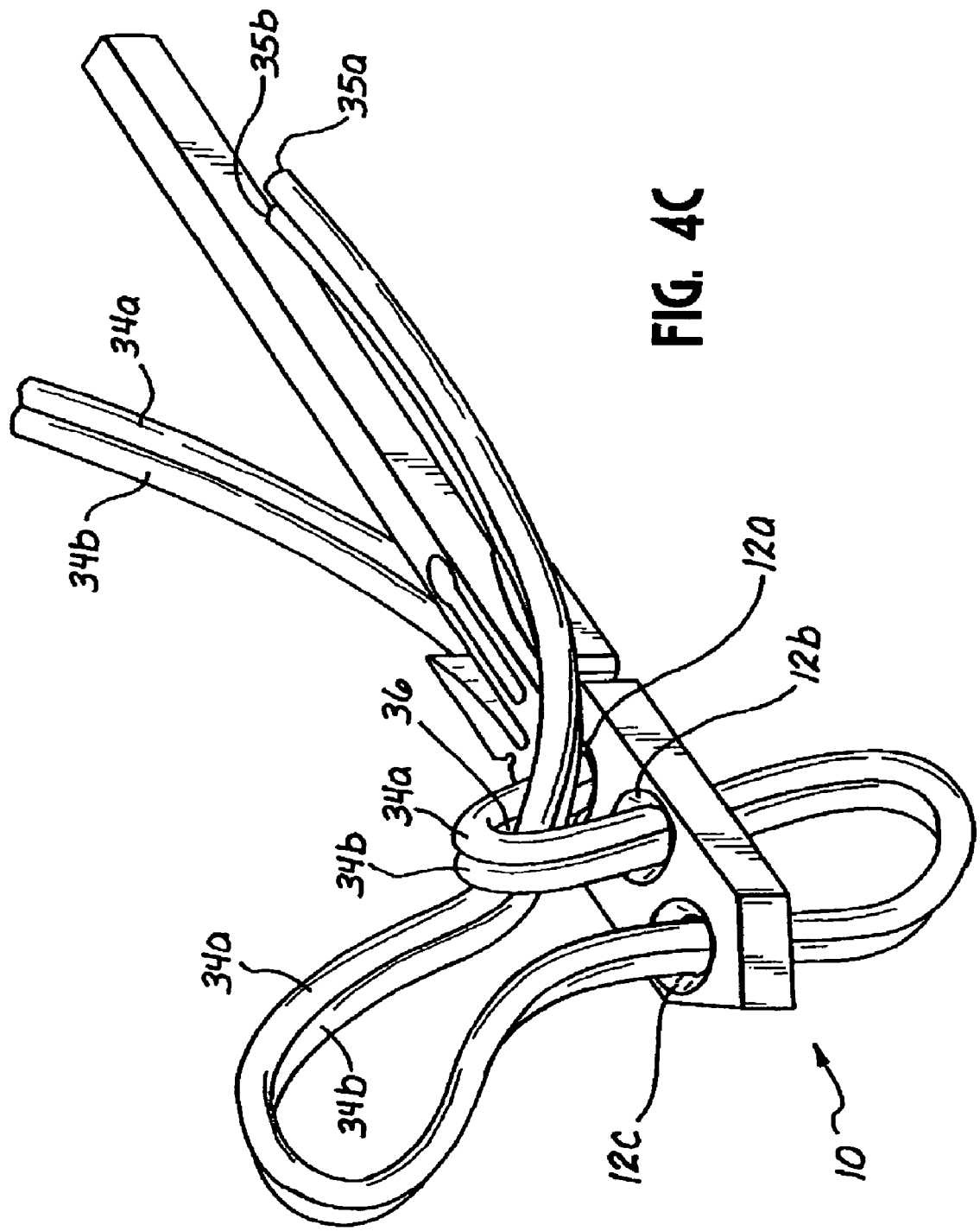

KNOTLESS SUTURE LOCK AND BONE ANCHOR IMPLANT METHOD

CROSS-REFENCE TO RELATED APPLICATIONS

This Application is a Continuation-in-part of commonly assigned U.S. patent application Ser. No. 10/690,438 filed on Oct. 21, 2003, now abandoned, herein incorporated by reference in its entirety for all purposes.

FIELD OF INVENTION

This invention in one aspect pertains to a knotless suture lock and bone anchor, in particular a knotless suture lock and bone anchor combination wherein a suture, looped through a tissue, is threaded through a plurality of body holes in the anchor to cinch the suture and tissue to the anchor without tying a suture knot on the tissue, and wherein the anchor is adapted for embedding in a bone.

BACKGROUND

This invention relates generally to methods and apparatus for attaching soft tissue to bone, and more particularly to anchors and methods for securing connective tissue, such as ligaments or tendons, to bone. In one aspect the invention has particular application to arthroscopic surgical techniques for reattaching the rotator cuff to the humeral head, in order to repair the rotator cuff.

It is an increasingly common problem for tendons and other soft, connective tissues to tear or to detach from associated bone. One such type of tear or detachment is a "rotator cuff" tear, wherein the supraspinatus tendon separates from the humerus, causing pain and loss of ability to elevate and externally rotate the arm. Complete separation can occur if the shoulder is subjected to gross trauma, but typically, the tear begins as a small lesion, especially in older patients. To repair a torn rotator cuff, the typical course today is to do so surgically, through a large incision. This approach is presently taken in almost 99% of rotator cuff repair cases. There are two types of open surgical approaches for repair of the rotator cuff, one known as the "classic open" and the other as the "mini-open". The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion. Because of this maneuver, the deltoid requires postoperative protection, thus retarding rehabilitation and possibly resulting in residual weakness. Complete rehabilitation takes approximately 9 to 12 months.

The mini-open technique, which represents the current growing trend and the majority of all surgical repair procedures, differs from the classic approach by gaining access through a smaller incision and splitting rather than detaching the deltoid. Additionally, this procedure is typically performed in conjunction with arthroscopic acromial decompression. Once the deltoid is split, it is retracted to expose the rotator cuff tear. As before, the cuff is debrided, the humeral head is abraded, and the so-called "transosseous tunnels", are "punched" through the bone or suture anchors are inserted. Following the suturing of the rotator cuff to the humeral head, the split deltoid is surgically repaired.

Although the above described surgical techniques are the current standard of care for rotator cuff repair, they are associated with a great deal of patient discomfort and a lengthy recovery time, ranging from at least four months to one year or more. It is the above-described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally and an anchor is driven into bone at a location appropriate for repair. Rather than thread the suture through transosseous tunnels, which are difficult or impossible to create arthroscopically using current techniques, tying the cuff down against bone using the anchor and suture completes the repair. Early results of less invasive techniques are encouraging, with a substantial reduction in both patient recovery time and discomfort.

Unfortunately, the skill level required to facilitate an entirely arthroscopic repair of the rotator cuff is inordinately high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of bone anchors to provide a suture fixation point in the bone, the knots that secure the soft tissues to the anchor by necessity leave the knot bundle on top of the soft tissues. In the case of rotator cuff repair, this means that the knot bundle is left in the shoulder capsule where the patient can feel it postoperatively when the patient exercises the shoulder joint. So, knots tied arthroscopically are difficult to achieve, impossible to adjust, and are located in less than optimal areas of the shoulder. Suture tension is also impossible to measure and adjust once the knot has been fixed. Consequently, because of the technical difficulty of the procedure, presently less than 1% of all rotator cuff procedures is of the arthroscopic type, and is considered investigational in nature.

Another significant difficulty with current arthroscopic rotator cuff repair techniques are shortcomings related to currently available suture anchors. Suture eyelets in bone anchors available today, which like the eye of a needle are threaded with the thread or suture, are small in radius, and can cause the suture to fail at the eyelet when the anchor is placed under high tensile loads.

There are various bone anchor designs available for use by an orthopedic surgeon for attachment of soft tissues to bone. The basic commonality between the designs is that they create an attachment point in the bone for a suture that may then be passed through the soft tissues and tied, thereby immobilizing the soft tissue. This attachment point may be accomplished by different means. Screws are known for creating such attachments, but suffer from a number of disadvantages, including their tendency to loosen over time, requiring a second procedure to later remove them, and their requirement for a relatively flat attachment geometry.

Another approach is to utilize the difference in density in the cortical bone (the tough, dense outer layer of bone) and the cancellous bone (the less dense, airy and somewhat vascular interior of the bone). There is a clear demarcation between the cortical bone and cancellous bone, where the cortical bone presents a kind of hard shell over the less dense cancellous bone. The aspect ratio of the anchor is such that it typically has a longer axis and a shorter axis and usually is pre-threaded with a suture. These designs use a hole in the cortical bone through which an anchor is inserted. The hole is drilled such that the shorter axis of the anchor will fit through the diameter of the hole, with the longer axis of the anchor being parallel to the axis of the drilled hole. After deployment in to the cancellous bone, the anchor is rotated 90° so that the long axis is aligned perpendicularly to the axis of the hole. The suture is pulled, and the anchor is seated up against the inside surface of the cortical layer of bone. Due to the mismatch in the dimensions of the long axis of the anchor and the hole diameter, the anchor cannot be retracted proximally from the hole, thus providing resistance to pull-out. These anchors still suffer from the aforementioned problem of eyelet design that stresses the sutures.

Still other prior art approaches have attempted to use a "pop rivet" approach. This type of design requires a hole in the cortical bone into which a split shaft is inserted. The split shaft is hollow, and has a tapered plug leading into its inner lumen. The tapered plug is extended out through the top of the shaft, and when the plug is retracted into the inner lumen, the tapered portion causes the split shaft to be flared outwardly, ostensibly locking the device into the bone.

Other methods of securing soft tissue to bone are known in the prior art, but are not presently considered to be feasible for shoulder repair procedures, because of physicians'0 reluctance to leave anything but a suture in the capsule area of the shoulder. The reason for this is that staples, tacks, and the like could possibly fall out and cause injury during movement. As a result of this constraint, the attachment point often must be located at a less than ideal position. Also, the tacks or staples require a substantial hole in the soft tissue, and make it difficult for the surgeon to precisely locate the soft tissue relative to the bone.

As previously discussed, any of the anchor points for sutures mentioned above require that a length of suture be passed through an eyelet fashioned in the anchor and then looped through the soft tissues and tied down to complete the securement. Much skill is required, however, to both place the sutures in the soft tissues, and to tie knots while working through a trocar under endoscopic visualization.

What is needed, therefore, is a new approach for repairing the rotator cuff or fixing other soft tissues to bone, wherein suture tension can be adjusted and possibly measured, the suture resides completely below the cortical bone surface, there is no requirement for the surgeon to tie a knot to attach the suture to the bone anchor, and wherein the procedure associated with the new approach is better for the patient, saves time, is uncomplicated to use, and easily taught to practitioners having skill in the art.

SUMMARY OF THE INVENTION

In one aspect the present invention solves the problems outlined above by providing innovative bone anchor and connective techniques which permit a suture attachment which lies beneath the cortical bone surface. In the present state of the art, the sutures which are passed through the tissues to be attached to bone typically are threaded through a small eyelet incorporated into the head of the anchor and then secured by tying knots in the sutures. Endoscopic knot tying is an arduous and technically demanding task. Therefore, the present invention discloses devices and methods for securing sutures to a bone anchor without the requirement of knot tying.

In one aspect of the invention, there is provided a bone anchor device for attaching connective tissue to bone, which comprises an anchor body, a plurality of suture retaining apertures disposed in the anchor body, and deployable structure for securing the anchor body in bone. The term "plurality of suture retaining apertures" means at least two, but three suture-retaining apertures are employed in the presently preferred embodiment.

A longitudinal axis is disposed along a center of the anchor body, wherein the plurality of suture retaining apertures are spaced axially relative to one another. Additionally, in preferred embodiments, at least two of the plurality of suture retaining apertures are transversely offset from one another relative to the longitudinal axis. Most preferably, a first of the at least two of the plurality of suture retaining apertures is disposed on one side of the longitudinal axis and a second of the at least two of the plurality of suture retaining apertures is disposed on the other side of the longitudinal axis. In other words, the two apertures are in a staggered orientation along the axis, with one on one side of the axis, and the other on the other side of the axis. The advantage of this configuration is that, as the suturing material is threaded through the axially spaced suture retaining apertures, because the apertures are offset from one another transversely, relative to the axis, the suturing material is wrapped in an angular orientation relative to the axis. This permits the suturing material to be wrapped over itself as it is threaded through the suture retaining apertures, in an "over and back" fashion, as will be described more fully hereinbelow.

In a preferred embodiment, the aforementioned deployable structure comprises a pair of deployable flaps. The anchor body comprises a substantially planar surface in which the plurality of suture retaining apertures is disposed. In its presently preferred embodiment, the anchor body comprises opposing substantially flat surfaces, wherein the plurality of suture retaining apertures extend through the entire anchor body. A stem extends proximally from a proximal end of the anchor body. At least a portion of a longitudinal slit is disposed in the stem.

In another aspect of the invention, a bone anchor device is provided for attaching connective tissue to bone. The bone anchor device comprises an anchor body having opposing substantially flat surfaces, deployable structure on a proximal end of the anchor body for securing the anchor body in bone; and a suture retaining aperture extending through the anchor body flat surfaces. The suture-retaining aperture is disposed distally of the deployable structure.

In yet another aspect of the invention, there is provided a bone anchor device for attaching connective tissue to bone, which comprises an anchor body having a distal end and a proximal end. A stem extends proximally from the proximal end of the anchor body. A deployable flap is disposed on the proximal end of the anchor body, and a notch on the anchor body is disposed at a location joining the anchor body and the deployable flap. The notch is adapted to cause the deployable flap to deploy outwardly when force is applied to a proximal end of the deployable flap by an actuator which moves distally relative to the deployable flap.

In another aspect of the invention, there is provided a bone anchor device for attaching connective tissue to bone. This inventive device comprises an anchor body having a distal end and a proximal end and a stem extending proximally from the proximal end of the anchor body. A deployable flap is disposed on the proximal end of the anchor body. The inventive device further comprises a slit, at least a portion of which is disposed in the stem.

In still another aspect of the invention, there is provided a bone anchor device for attaching connective tissue to bone. The inventive device comprises an anchor body having two opposing surfaces, and a suture retaining aperture disposed in the anchor body and extending through both of the opposing surfaces. A length of suturing material extends through the suture retaining aperture, wherein the length of suturing material is looped about the anchor body and contacts substantial portions of both of the two opposing surfaces. Advantageously, in order to fully lock the suturing material in place on the anchor body, a first portion of the length of suturing material is looped over a second portion of the length of suturing material, the second portion of which lies in contacting engagement with one of the opposing surfaces of the anchor body.

Preferably, a second suture-retaining aperture is disposed in the anchor body in axially spaced relation to the suture-retaining aperture, wherein the length of suture retaining material is looped through both of the suture retaining apertures.

In yet another aspect of the invention, there is disclosed a method for securing connective tissue to bone. This inventive method comprises a step of securing a first end of a length of suture to a portion of soft tissue to be attached to a portion of bone. A second end of the length of suture is threaded sequentially through a plurality of suture retaining apertures in a body of a bone anchor device so that the length of suture is securely fastened to the bone anchor body. The bone anchor body is placed in a blind hole disposed in the aforementioned portion of bone. Then, structure on the bone anchor body is deployed in an outward direction to secure the bone anchor body in the blind hole.

In a further aspect, the present suture lock and bone anchor combination is an embeddable bone anchor adapted to attach tissue to bone without a suture knot on the tissue by suturing the tissue without tying a suture knot on the tissue, and cinching the suture onto the anchor such that the anchor can be embedded into the bone to reattach the tissue to the bone. The loop is formed on the anchor by fixing the standing leg portion of the suture distally in the anchor and threading the working leg portion of the loop through holes in the anchor. On pulling on the working leg portion, the suture tightens on the anchor to cinch the loop and tissue to the anchor, without forming a knot on the tissue. The anchor is adapted such that, on embedding the anchor in the bone, the standing leg portion of the suture is located distally in the bone, and the working leg portion projects out of the bone. Barbs on the anchor resist pullout of the anchor from the bone; the barbs also increase the frictional force on the suture in the bone to maintain the integrity of the loop.

In one embodiment, the present suture lock and bone anchor comprises a body structure comprising a plurality of body holes adapted to thread a suture through the body structure; a suture leg-anchoring structure adapted to fasten a standing leg portion of the suture onto the anchor; and a bone-embedding structure adapted to embed the anchor in a bone, wherein a tissue can be cinched to the anchor by suturing the tissue without tying a knot on the tissue, attaching the standing leg portion of the suture onto the leg-anchoring structure, threading the working the portion of the suture through the body holes, and pulling on the working leg portion of the suture.

In another embodiment the present suturing lock and bone anchoring system is a suture lock and bone anchoring system comprising: a embeddable anchor body structure comprising a plurality of body holes adapted for threading a suture therethrough; a suture leg-anchoring structure disposed distally of the body structure; and a suture having a standing leg portion and a working leg portion threaded through the body holes, wherein the standing leg portion of the suture is attached to the suture leg-anchoring structure, and the working leg portion is cinchable onto the body structure by pulling on the working leg portion through the body holes.

In another embodiment the present suture lock and bone anchor comprises a method of anchoring tissue to bone, comprising: passing a length of suture through the tissue to obtain a standing leg portion and a working end portion of suture; attaching the standing end portion of the suture to a suture leg-anchoring structure on a bone anchor, the bone anchor comprised of a distal section and a proximal section; threading the working end portion of the suture through a plurality of body holes in a body structure of the anchor to form a cinchable suture loop on the anchor proximally of the suture leg-anchoring structure; and imbedding the bone anchor in a bone such that the standing leg is oriented distally of the anchor body.

The invention, together with additional features and advantages thereof, may best be understood by reference to the following description taken in conjunction with the accompanying illustrative drawing.

BRIEF DESCRIPTION OF THE DRAWINGS

FIG. 1 is a plan view of a presently preferred embodiment of the inventive bone anchor device;

FIG. 1A is a plan view of the inventive bone anchor device illustrated in FIG. 1, wherein the stem of the device has been inserted into a hollow casing;

FIGS. 5A-5I are diagrammatic plan views, in sequence, illustrating one preferred method of using the inventive bone anchor device in the attachment of soft tissue to bone, in this case, the repair of a torn rotator cuff;

DETAILED DESCRIPTION

Figure 2:
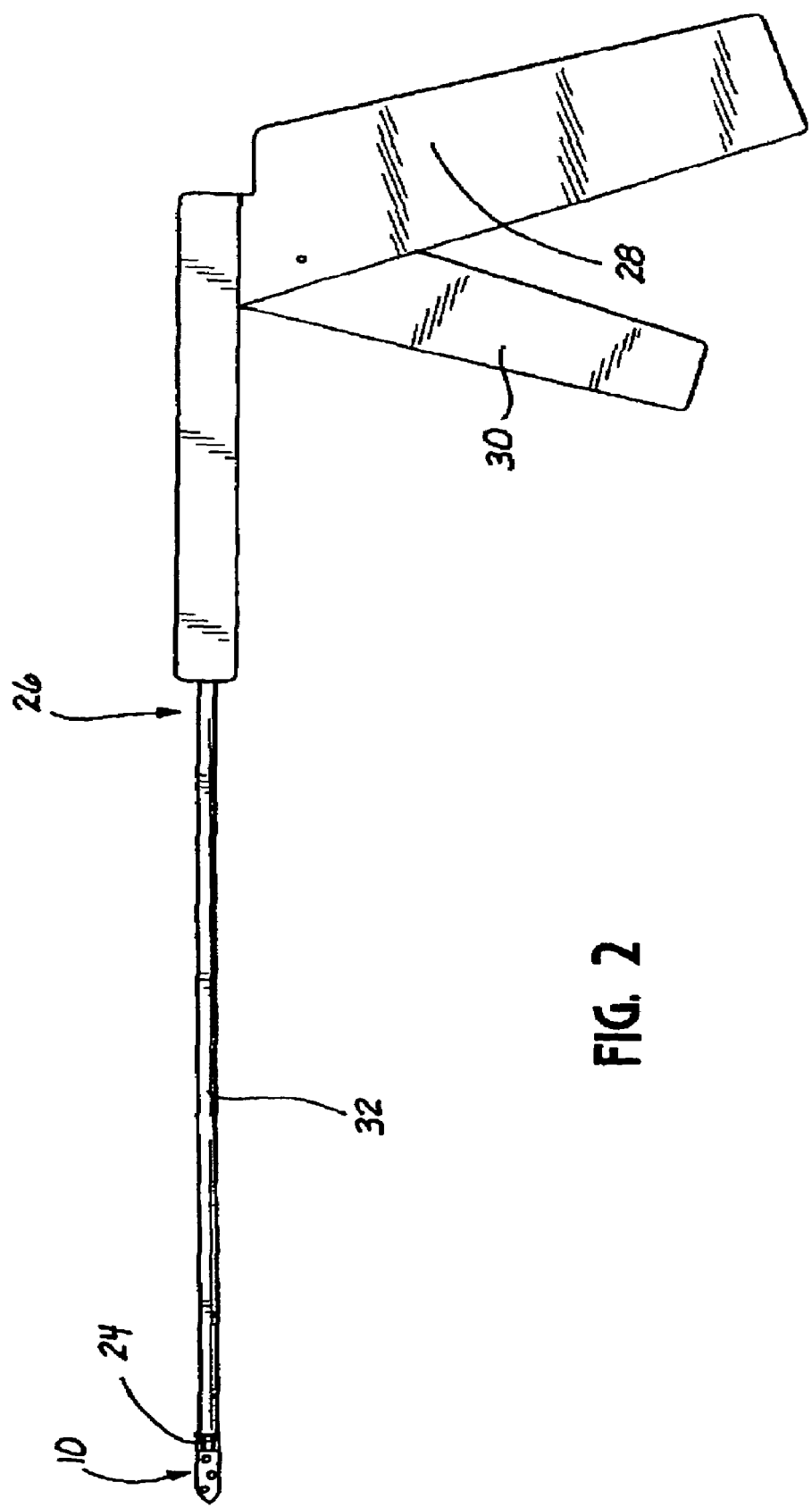
FIG. 2 is a plan schematic view illustrating a preferred deployment system for a bone-anchoring device of the type shown in FIGS. 1 and 1A.

Referring now more particularly to the drawings, there is shown in FIG. 1 a bone anchor 10 in its undeployed state. The distal end of the bone anchor 10 is comprised of a substantially flat body 11 which preferably has three eyelet holes or suture retaining apertures 12a, 12b, and 12c, and which comes to a point 13 at a distal end where it is to be inserted into the bone. Two deployable flaps 14a, 14b are defined by two notches 16a,b which allow for deployment of the flaps, and are disposed at a point where the flaps 14a, 14b are attached to the flat body 11. To a proximal end of the bone anchor is joined a relatively narrow stem 18. A slit 20 is disposed at least partially on the stem 18 and partially on the flat body 11, although in presently preferred embodiments, the slit 20 is disposed entirely on the stem 18, as shown in FIG. 1. Weak links 22a, 22b are formed on either side of the slit 2.

As shown in FIG. 1a, the proximal end of the stem 18 of the bone anchor 10 is preferably inserted into a hollow casing 24, which in turn has been attached to the stem 18 utilizing methods well known in the art such as crimping, welding or the like, in order to secure the bone anchor 10 to the casing 24. The casing 24 is intended to provide an easy means for insertion of the bone anchor apparatus 10 into a deployment device for deploying the bone anchor as shall be more fully described and illustrated hereinbelow. It is to be understood, of course, that the flat form of the bone anchor 10 and the shape of the casing 24 are used herein for informational purposes as to possible methods of fabrication only, and are not to be deemed limiting.

Referring now to FIG. 2 there is illustrated a deployment device 26 which may, for example, be used to deploy the bone anchor 10. This representative deployment device 26 includes a handle 28, a trigger 30, and a hollow barrel 32 into which the casing 24 on the proximal end of the bone anchor 10 has been inserted for deployment. Although many methods of deployment may be utilized, in the deployment device 26 herein illustrated, the proximal end of the casing 24 is coupled to the trigger mechanism 30 through the barrel 32 of such deployment device 26. When the trigger mechanism 30 is activated, the proximal end of the casing 24 is pulled into the hollow barrel 32 until the distal end of the hollow barrel 32 comes into contact with the flaps 14a, 14b on the bone anchor 10, thus applying a distally-directed force thereon and thereby deploying such flaps 14a, 14b, as shall be shown and described below.

Figure 3A:
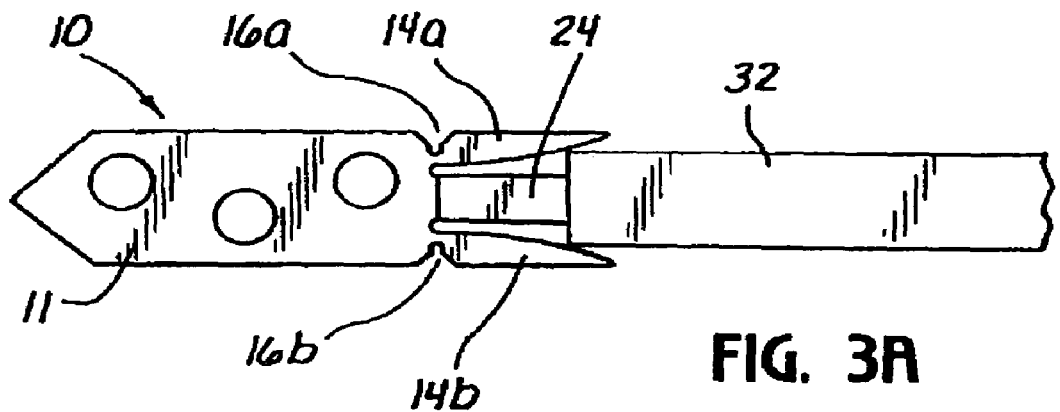
FIGS. 3A-3C are plan views similar to those of FIGS. 1 and 1A, illustrating in sequence a preferred method for deploying the bone anchor device of the present invention.
Figure 3B:
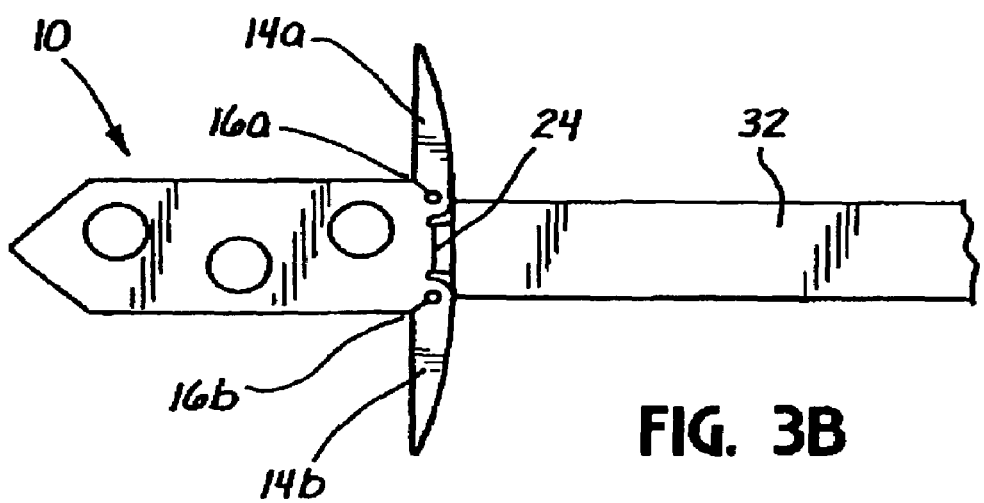
Figure 3C:
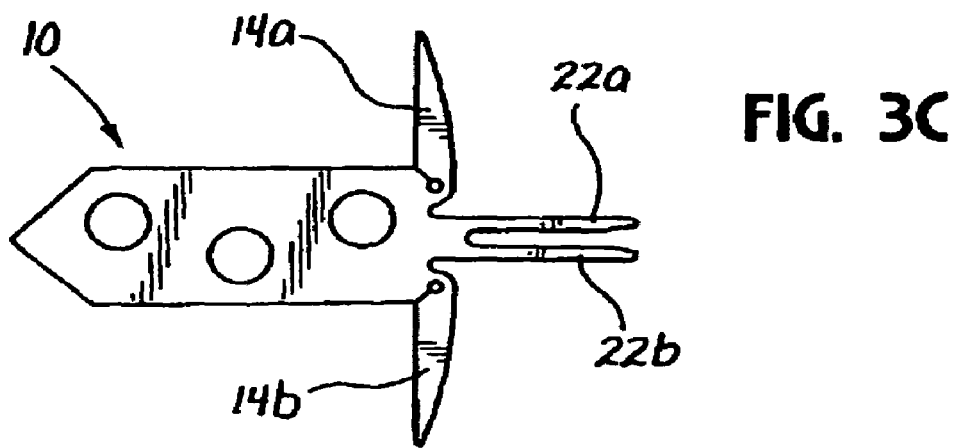

Referring now to FIG. 3A, the casing 24 that has been crimped or otherwise attached to the bone anchor 10 is shown inserted into the barrel 32 of the deployment device 26 (FIG. 2) before deployment of the anchor flaps 14a, 14b. As seen in FIG. 3B, the barrel 32 is driven in a distal direction (or, preferably, the casing 24 is drawn into the barrel 32), which causes the distal end of the barrel 32 to come into contact with flaps 14a, 14b. By continuing to move the barrel 32 distally, relative to the flaps 14a, 14b, once the aforementioned contact has been made, force will be applied against the base of each flap, causing each flap to bend outwardly at its respective notch 16a, 16b as shown in FIG. 3B. The result is that the flaps 14a, 14b are deployed outwardly from the body of the bone anchor 10.

As the deployment force exerted by the barrel 32 is taken directly on the face of the flaps 14a, 14b, as noted supra, the notches 16a, 16b close and limit the bending of the flaps 14a, 14b, and the load on the weak links 22a, 22b on opposing sides of the slit 20 begins to increase as a result of the imposition of a tensile force on the proximal end of the bone anchor after the distal end thereof has been anchored into the bone. In other words, because the anchor body 11 is fixed in the bone, and cannot move responsive to the applied tensile force, the reactive force applied by the anchor body on the stem 18 causes the weak links 20a, 20b to fracture, thereby separating the casing 24 and the broken stem 18 from the bone anchor 10, leaving the bone anchor 10 anchored into the bone structure.

Figure 4R:
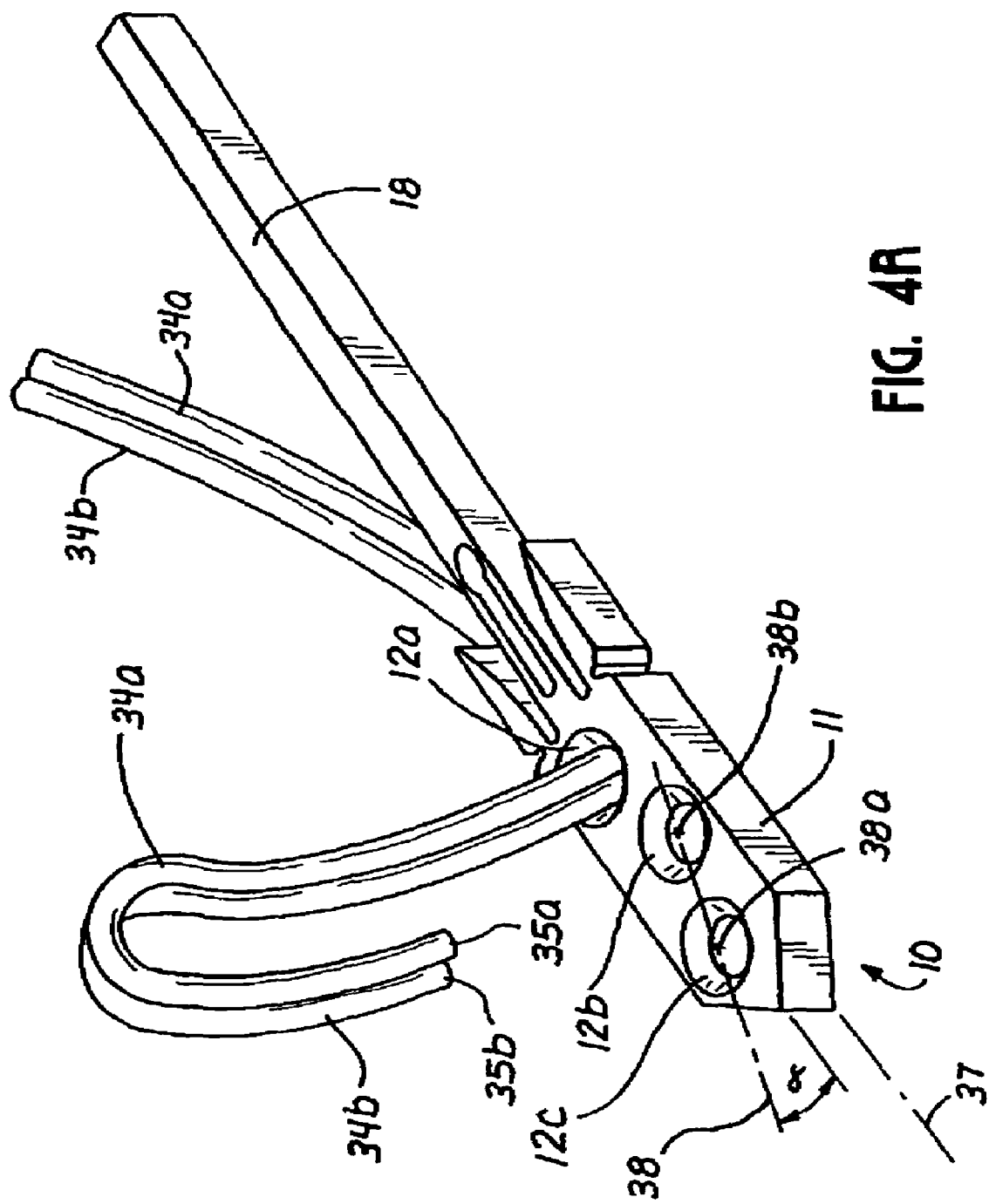
FIGS. 4A-4E are perspective views of the inventive bone anchor device shown in FIGS. 1-3C, illustrating in sequence a preferred method for threading the device with suturing material.
Figure 4B:
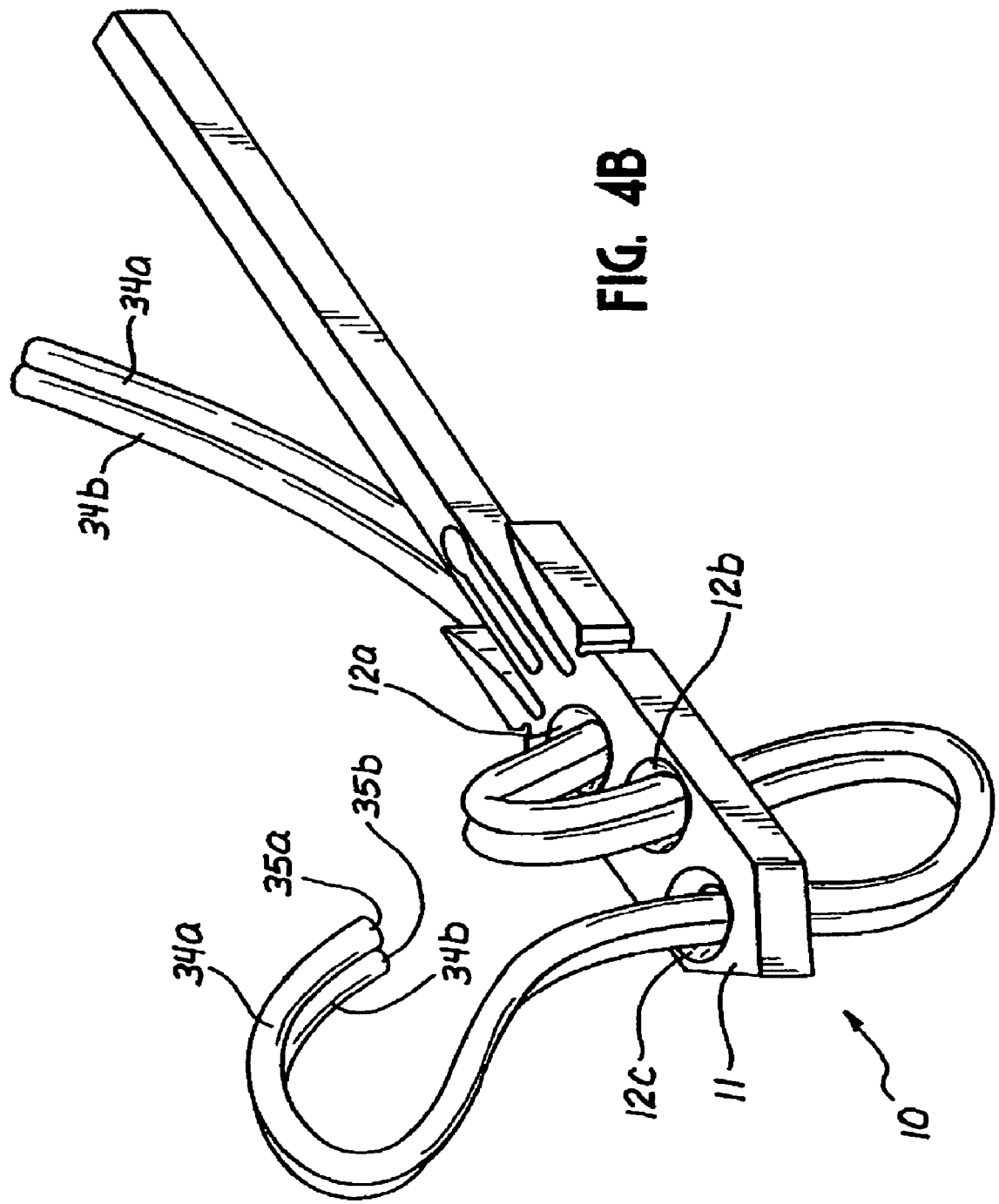

Referring to FIGS. 4a-4e, it may be seen how suture may be attached to the bone anchor apparatus 10, in accordance with one preferred method, prior to its deployment into the bone structure. As illustrated in FIG. 4a, adjacent lengths of suture 34a, 34b have two corresponding free ends 35a, 35b, respectively, which have already been disposed through a tendon or portion of soft tissue (not shown), and then are passed from the underside of the bone anchor 10 in its undeployed state through the eyelet hole 12a. In actuality, as will be explained in more detail hereinbelow, the two suture lengths 34a, 34b represent the free ends of a length of suture which has been looped through a portion of soft tissue in the form of a mattress stitch. In FIG. 4b, the suture lengths 34a, 34b are then threaded from the top side of the bone anchor body 11 through the eyelet 12b to the underside of the anchor body 11, and then back up to the top side thereof through the eyelet hole 12c. In FIG. 4c the loose or free ends 35a, 35b of the suture lengths 34a, 34b, respectively, are passed, as illustrated, through a loop 36, which is formed by a portion of the lengths of suture 34a, 34b, on the top side of the bone anchor between eyelet holes 12a,b.

An important feature of the present invention concerns the placement of the suture retaining apertures or eyelet holes 12a, 12b, and 12c. As illustrated in FIG. 4a, the bone anchor 10 of the present invention has a longitudinal axis 37 extending along its axial center. In the illustrated preferred embodiment, each of the suture retaining apertures 12, 12b, and 12c are axially spaced and are offset from the longitudinal axis in a transverse direction (meaning the direction orthogonal to the axis). This offset can be measured by measuring the distance from the longitudinal axis 37 to a center of the suture-retaining aperture. More preferably, successive suture retaining apertures (i.e. 12a and 12b or 12b and 12c) are offset in a "staggered" fashion, meaning they are offset from the longitudinal axis in opposed transverse directions. The purpose for this offset is to ensure that the suturing material, as it is threaded through the apertures in a distal direction (FIG. 4b), and then returned in a proximal direction beneath the loop 36 (FIG. 4c), lies at an angle relative to the longitudinal axis 37. Without this angled orientation, the suture loop lock feature of the invention would not be as easy to achieve, nor as effective.

In one presently preferred embodiment, as illustrated in FIGS. 1 and 4a, an angle a between a line 38 which lies between a center point 38b of aperture 12b and a center point 38c of aperture 12c, and the longitudinal axis 37 preferably falls within a range of approximately 10-30 degrees, and is most preferably about 18-25 degrees. In the preferred embodiment shown, the angle a is between 19 and 20 degrees. The inventor has found that if the angle $\alpha$ is too great, improper suture locking may occur, and, conversely, there may be an inadequate ability to adjust the suture once it has been threaded about the anchor body.

Additionally, as shown in FIG. 1, in the presently preferred embodiment, the distance x between a centerline 38d running between center points 38a and 38c of apertures 12a and 12c and a centerline 38e running through center point 38b of aperture 12b is approximately 0.035 inches. A distance y from the axis 37 to the centerline 38d is 0.0175 inches in the same preferred embodiment, which, of course, means that the aperture 12b is equally offset 0.0175 inches from the axis 37 in the opposing transverse direction. Of course, these specific distances are merely exemplary, and are not required for successful implementation of the inventive concept. For example, they may be scaled to differently sized instruments. It is also possible to implement the invention without utilizing suture retaining apertures which are equally spaced from the longitudinal axis 37, or which are offset from the axis 37 at all. Such an embodiment is shown, for example, in FIG. 7, which will be discussed hereinbelow.

Figure 4D:
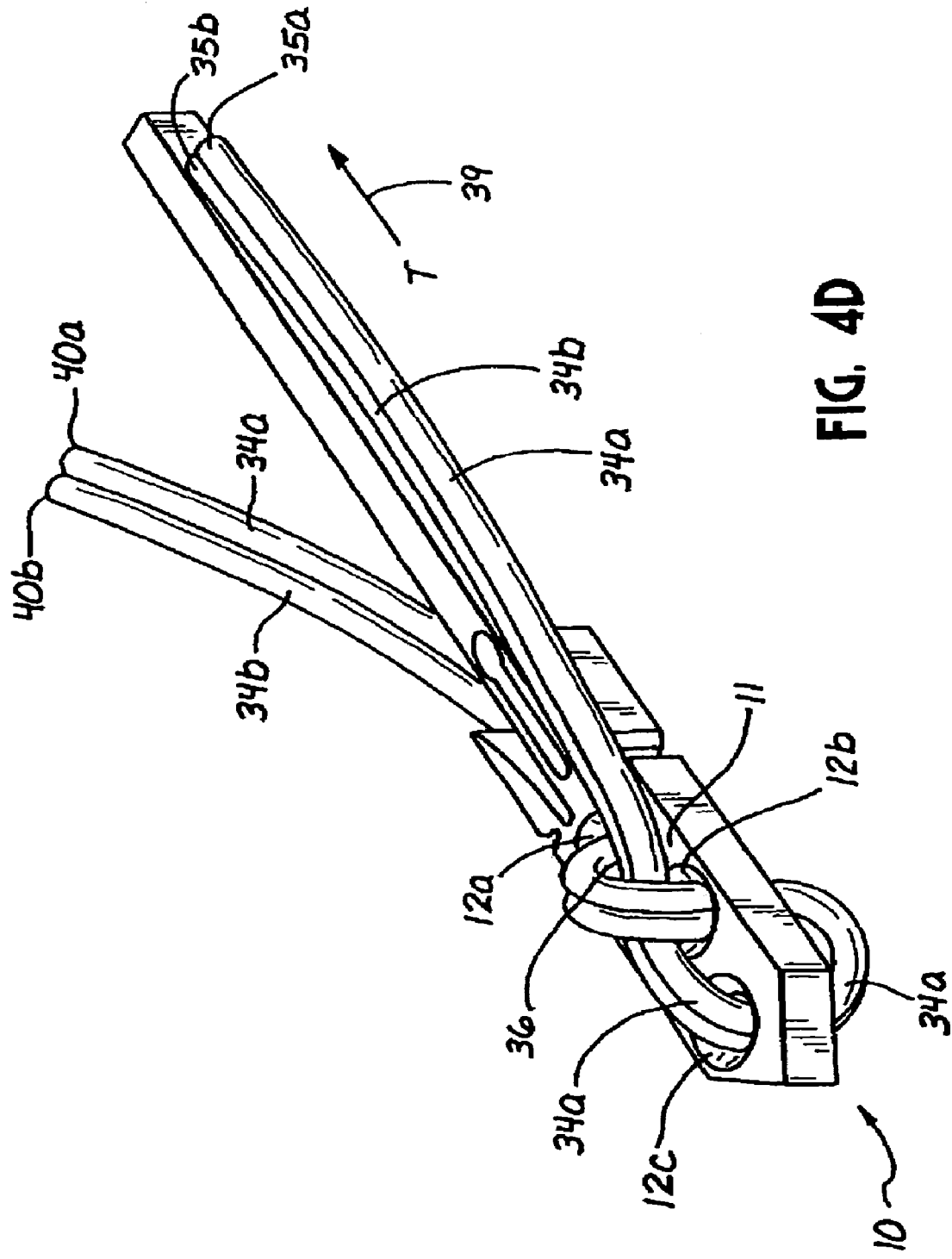
Figure 4E:
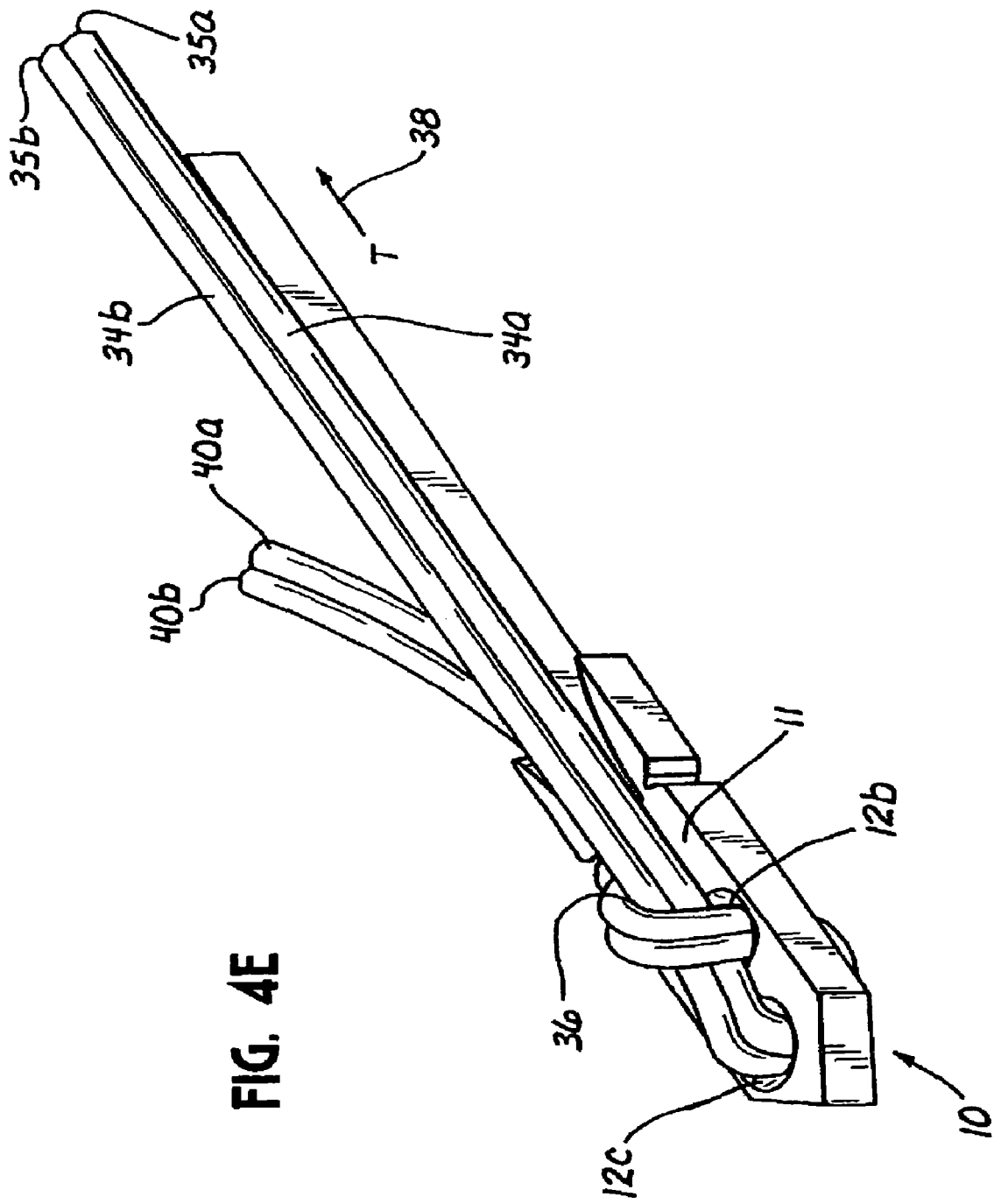

In FIGS. 4d and 4e, the free ends 35a, 35b of the suture lengths 34a, 34b, respectively, are drawn snugly by creating a tension as represented by the letter T in the direction of the arrow 39 in order to eliminate any slack at the fixation point of the suture lengths 34a, 34b to the bone anchor 10 as well as to create tension in the suture lengths 34a, 34b that is disposed, in turn, through the tendon or soft tissue to be attached to bone by the bound ends 40a, 40b, respectively, of the suture lengths 34a, 34b. It is to be understood that it is the combination of the tension in the suture lengths 34a, 34b and the passing of the suture lengths 34a, 34b beneath the loop 36 that defines the inventive locking aspect of the invention. It may be seen that as the tension in the suture lengths 34a, 34b is increased on the free ends 35a, 35b, respectively, the suture lengths 34a, 34b are drawn through the eyelets 12a, 12b, 12c and through the loop 36, creating greater and greater tension on the bound legs 40a, 40b, which by direct contact through the suture loop 36, locks the free suture lengths 34a, 34b against the flat body 11 of the bone anchor 10.

It is to be understood, of course, that while we have been talking about a preferred case of two free lengths 34a, 34b of suture which extend from two bound ends 40a, 40b thereof, wherein the bound ends are actually the two opposing ends of a loop of suture extending through a portion of soft tissue in the form of a mattress stitch, this invention is equally well adapted to the use of a single length of suture, or a plurality of lengths of suture greater than two, if desired.

Referring now to FIGS. 5a-5i, it can be seen more particularly how the inventive apparatus may be utilized, in one preferred procedure, as a bone anchor for the attachment of soft tissues to bone. It should be noted, in this respect, that those elements which are common to elements shown in FIGS. 1-4e are designated by common reference numerals. Now, in FIG. 5a there is shown a cross-sectional view of a human shoulder on the left side of the body as seen from the front of the body and which illustrates a rotator cuff tendon 46 which is disposed across a humeral head 48. It is to be understood that, in this illustration, the rotator cuff tendon is detached from the humeral head 48 at the interface 50 between the two. This is the problem which is to be corrected by the inventive procedure. The humeral head 48 is comprised of an outer surface of cortical bone 52 and inner cancellous bone 54. To allow for arthi-oscopic access, a trocar 56 has been inserted into the shoulder in proximity to the area where the rotator cuff tendon 46 is to be reattached to the humeral head 48, and a hole 58 has been made, preferably by drilling or punching, in the desired location through the cortical bone 52 and into the cancellous bone 54. This illustration is intended only to provide a simple structural overview of the physiological elements involved in a typical situation where it is to be desired that soft tissue such as a rotator cuff tendon 46 be reattached to a humeral head 48. However, it should be clear that the inventive procedure may be used in other areas of the body where soft tissue is to be reattached to bone.

Alternate rotator cuff repair procedures are also discussed in co-pending U.S. patent application Ser. No. 09/475,495, filed on Dec. 30, 1999, and entitled Method and Apparatus for Attaching Connective Tissues to Bone Using a Knotless Suture Anchoring Device, which is herein expressly incorporated by reference.

Figure 5A:
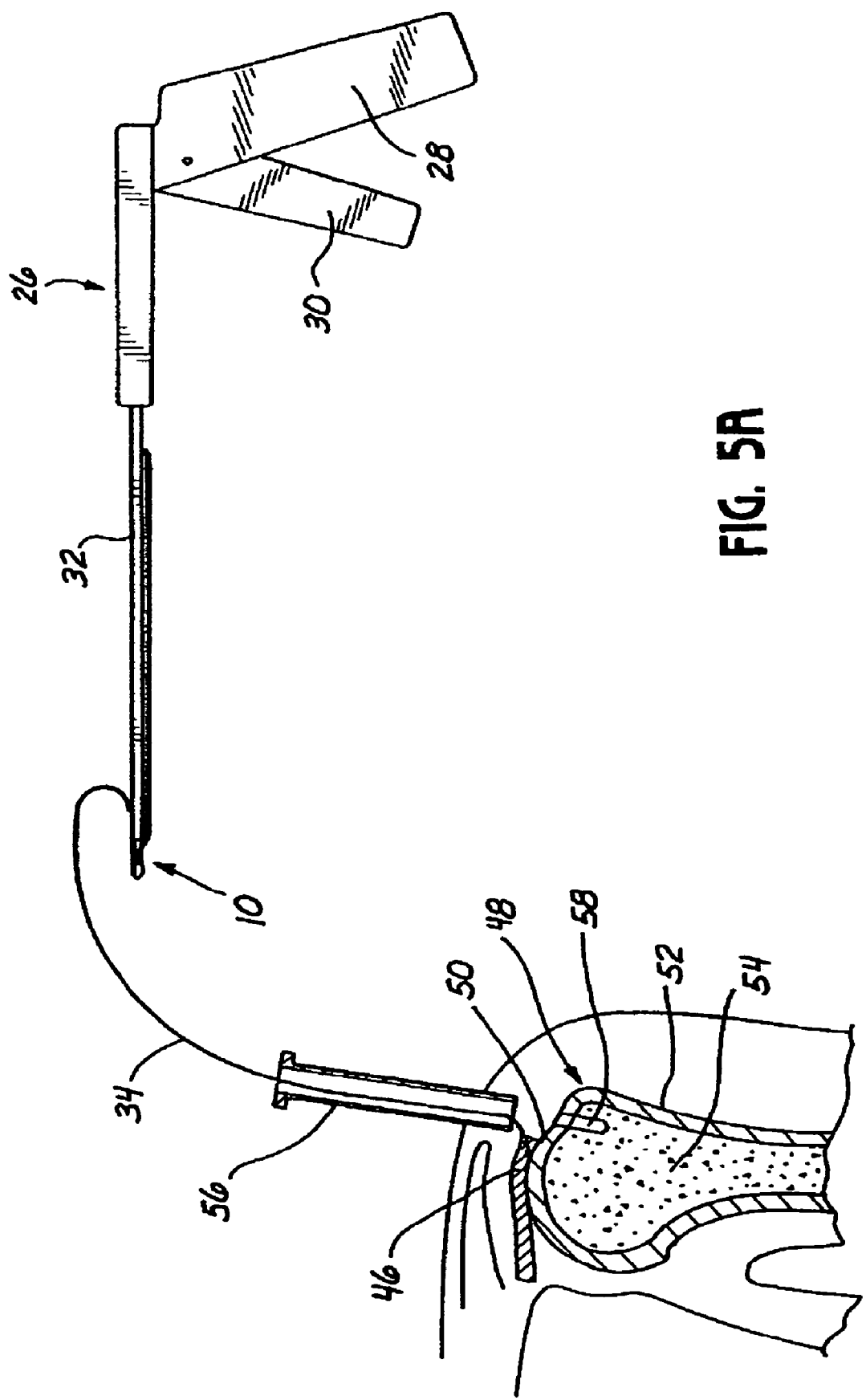

Referring still to FIG. 5a it can be seen that a length of suture 34 has been passed through the tendon 46 with the loose or free ends of the suture passing through the trocar and out of the shoulder. This step of suturing the tendon 46 is beyond the scope of the present application, but any known technique may be utilized. The present invention is particularly suited, however, to the use of a suturing instrument, as described in co-pending U.S. patent application Ser. No. 09/668,055, entitled Linear Suturing Apparatus & Methods, filed on Sep. 21, 2000, which is commonly assigned with the present application and is herein expressly incorporated by reference. This type of suturing instrument will produce a "mattress stitch" through the tendon 46, which is a preferred stitch for most practitioners. The free ends of the suture 34 have been threaded through the bone anchor 10 as previously described in connection with FIGS. 4a-c, above, and the proximal end of the bone anchor 10 has been inserted into the barrel 32 of the deployment device 26 as also previously described in connection with FIG. 2, above.

Figure 5B:
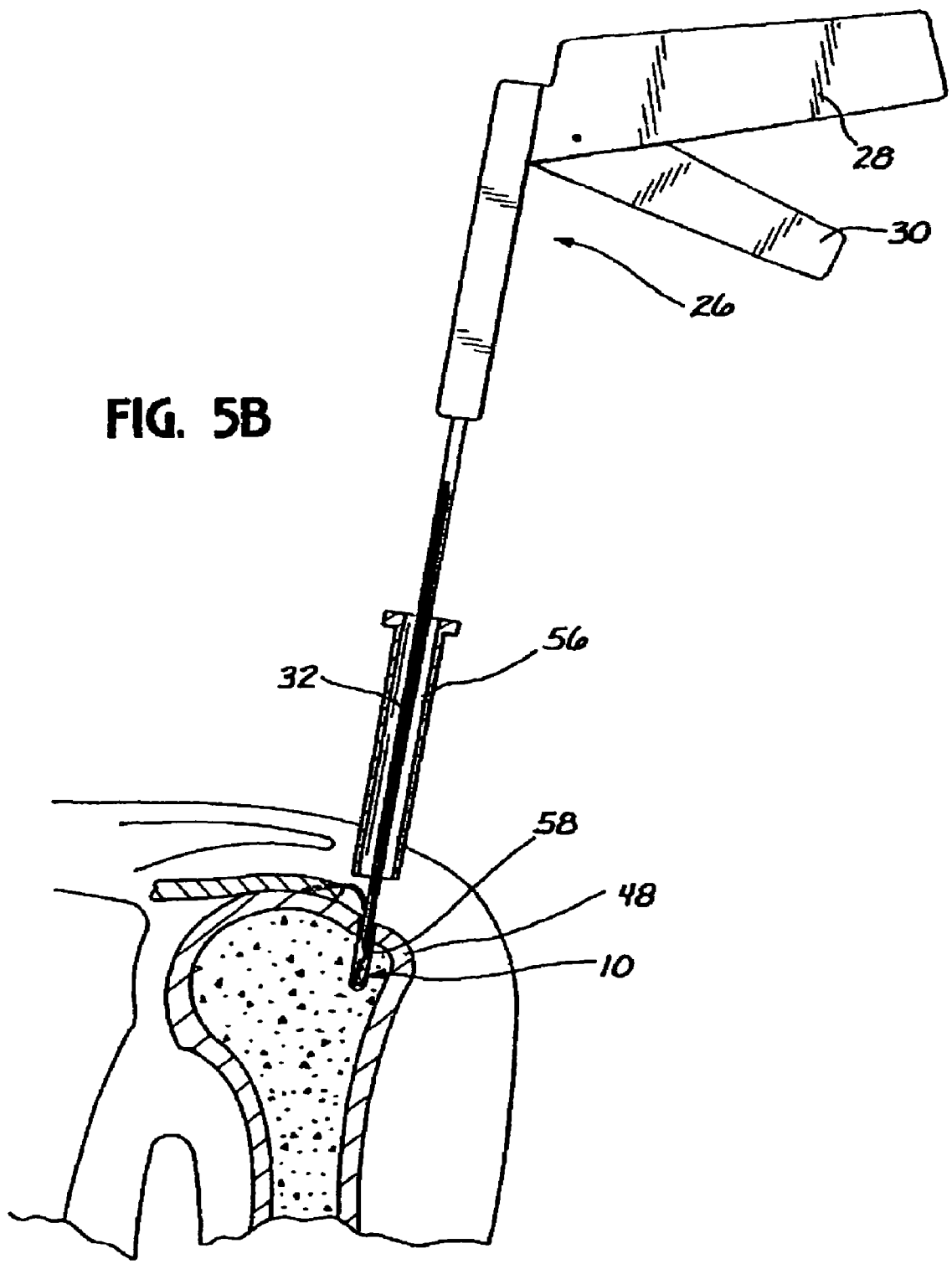

FIG. 5b illustrates in enlarged detail how the bone anchor 10 is inserted through the trocar 56 by means of the barrel 32 of the deployment device 26 and into the hole 58 which has been made in the humeral head 48.

Figure 5C:
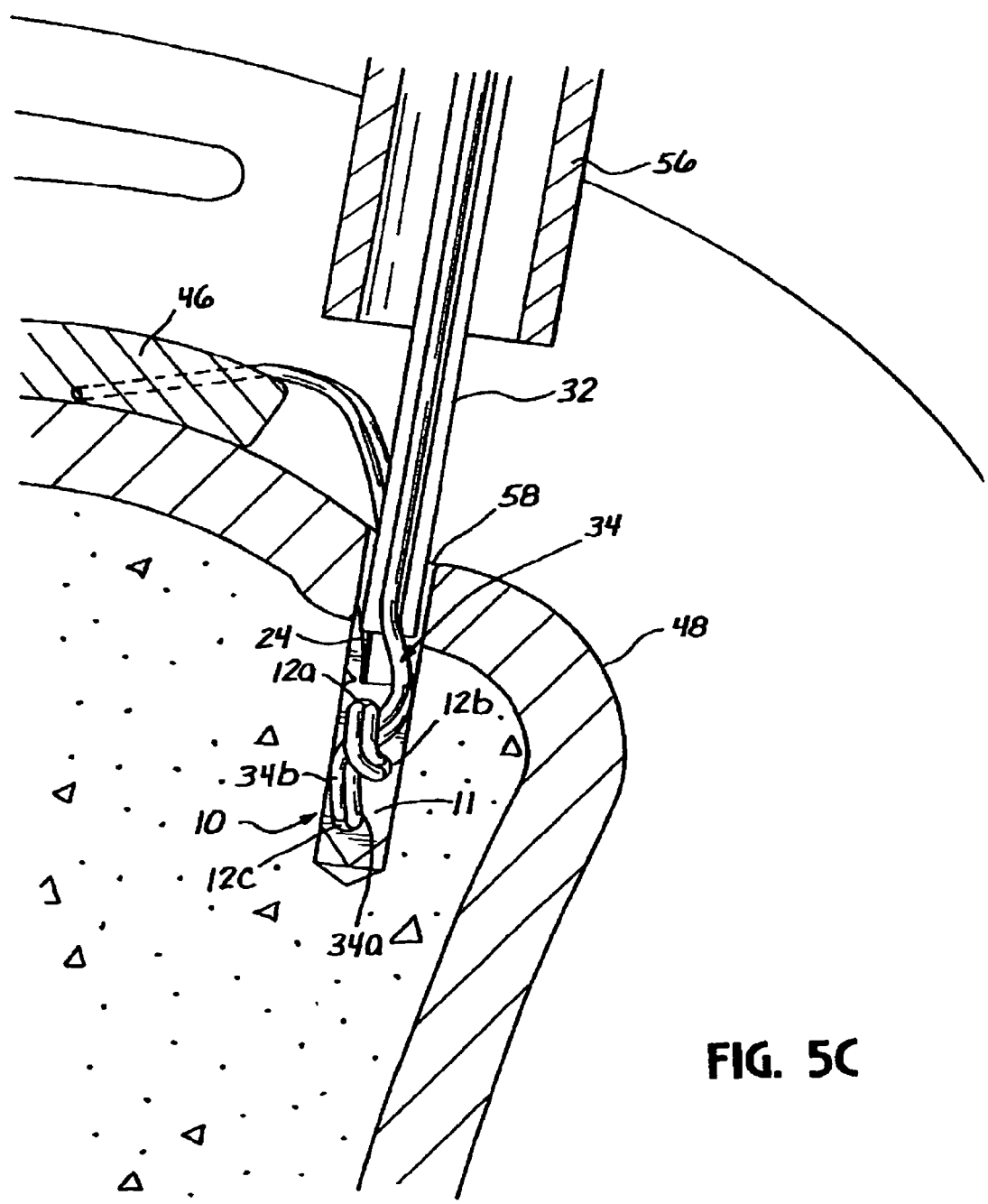

In FIG. 5c a further enlarged view of the same general illustration is provided, detailing the distal end of the instrument and the procedural site. It can be seen in this view that each free leg 34a, 34b of the suture 34 has been drawn tight against the bone anchor 10 by applying continual tension to the free ends 35a, 35b (not shown—they extend proximally out through the barrel 32) of the suture 34 as the bone anchor is inserted through the trocar 56 and into the hole 58 in the humeral head 48.

Figure 5D:
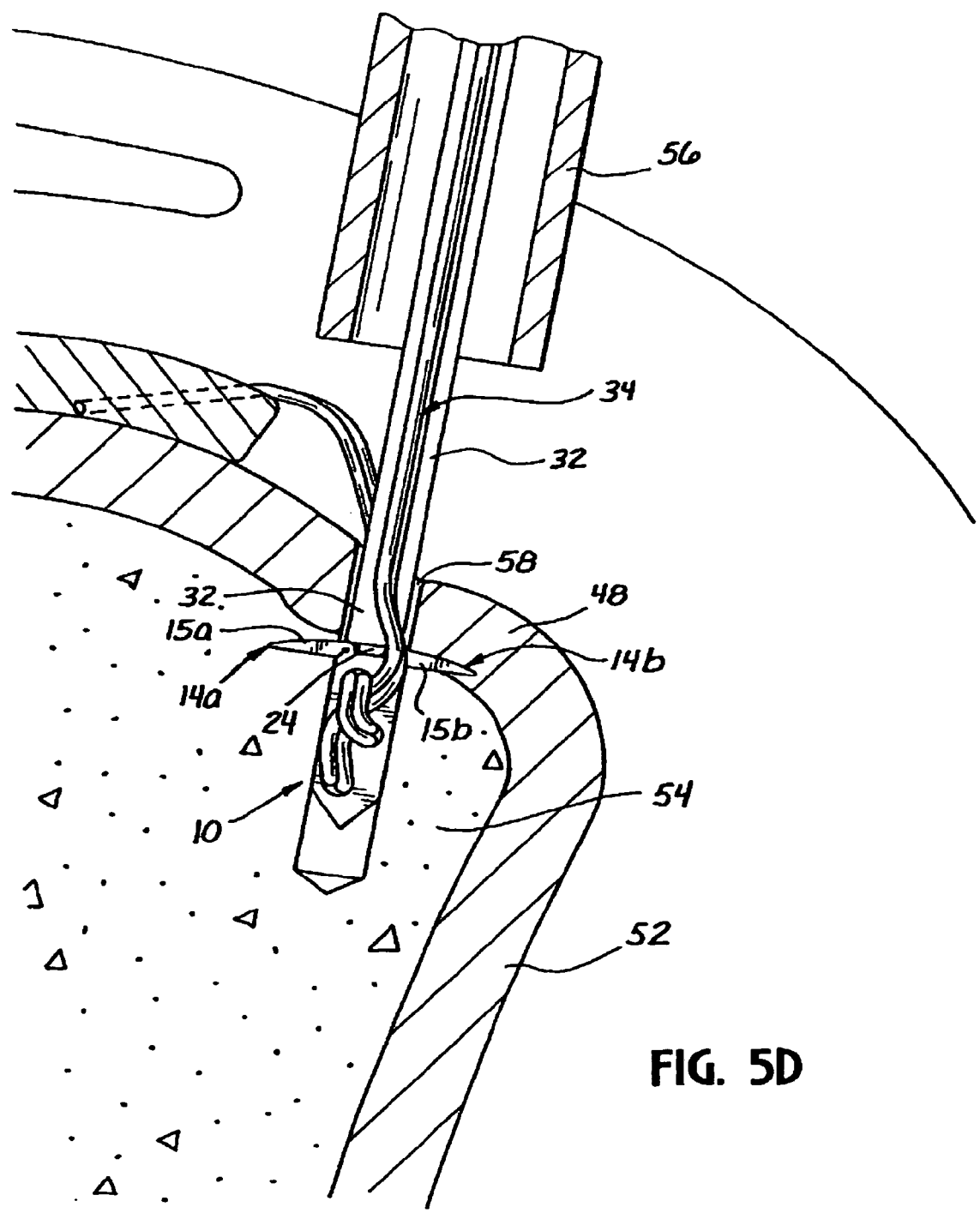

The bone anchor of FIG. 5c is still in its undeployed state. In FIG. 5d the bone anchor device has been deployed by activating the trigger mechanism of the deployment device 26 as illustrated in FIG. 2 and described above. Activation of such triggering mechanism causes the casing 24 which is attached to the proximal end of the bone anchor 10 to be pulled proximally into the barrel 32 of the deployment device. As the bone anchor is pulled into the barrel 32 the flaps 14a, 14b of the bone anchor impact against the end of the barrel 32, deploying such flaps outward from the bone anchor 10 in proximity to the interface of the cortical bone 52 and the cancellous bone 54. The flaps 14a, 14b bear against the inside of the cortical bone 52, thereby preventing the bone anchor from being retracted proximally out of the hole 58 in the cortical bone 52. Any rotational moment is also resisted by the flaps 14a, 14b, and more specifically by the edges 15a, 15b of the flaps 14a, 14b.

Figure 5E:
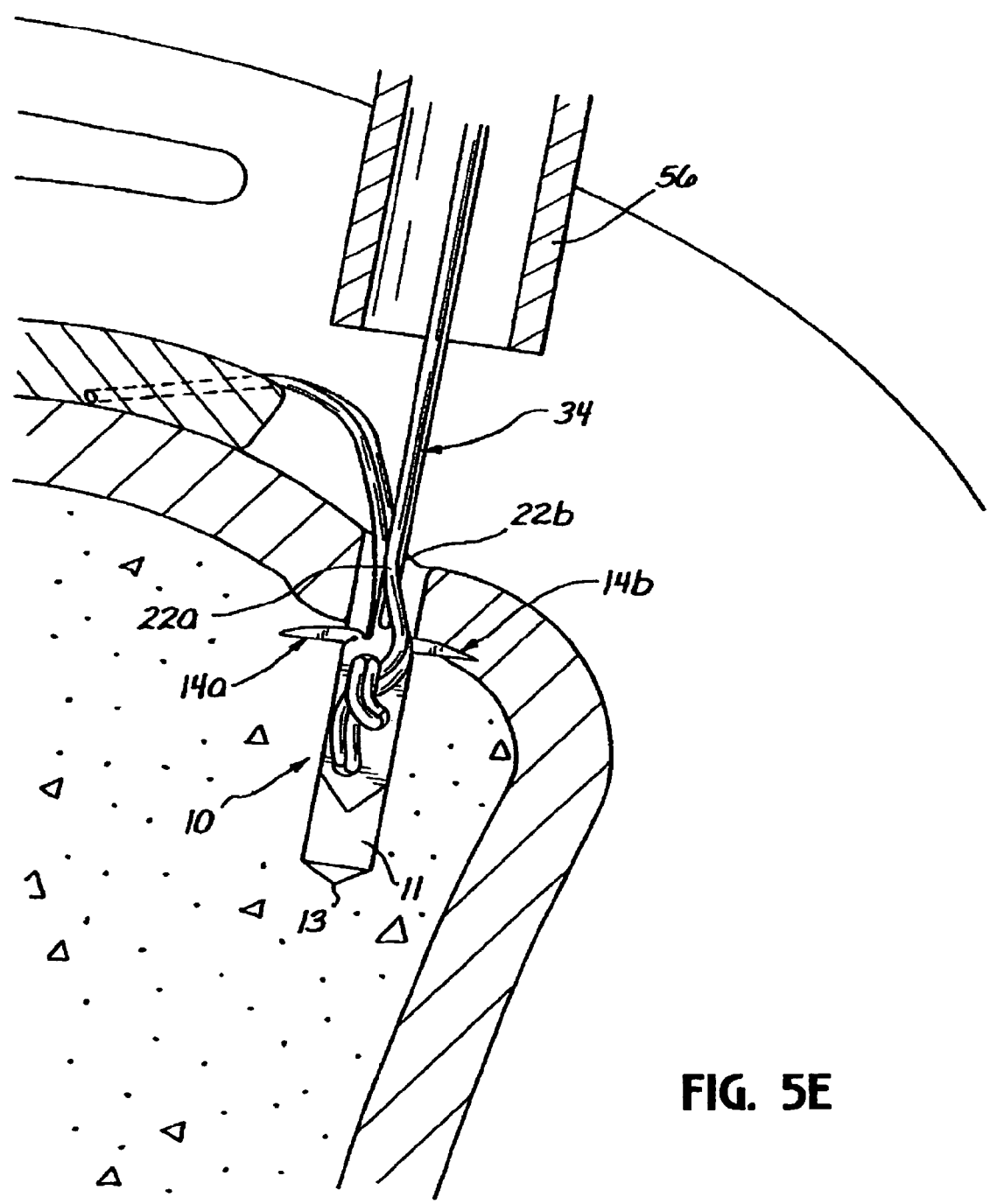

In FIG. 5e the barrel 32 of the deployment device has been removed from the trocar 56 by withdrawing it proximally through such trocar. As previously described in connection with FIGS. 3a through 3c, the tension imposed on the casing which is attached to the bone anchor stem as illustrated in FIG. 1a, causes the weak links 22a, 22b to break, thereby separating the casing 24 from the bone anchor 10 and allowing the casing to be removed and discarded, and leaving the bone anchor 10 permanently disposed within the cancellous bone of the shoulder.

Figure 5F:
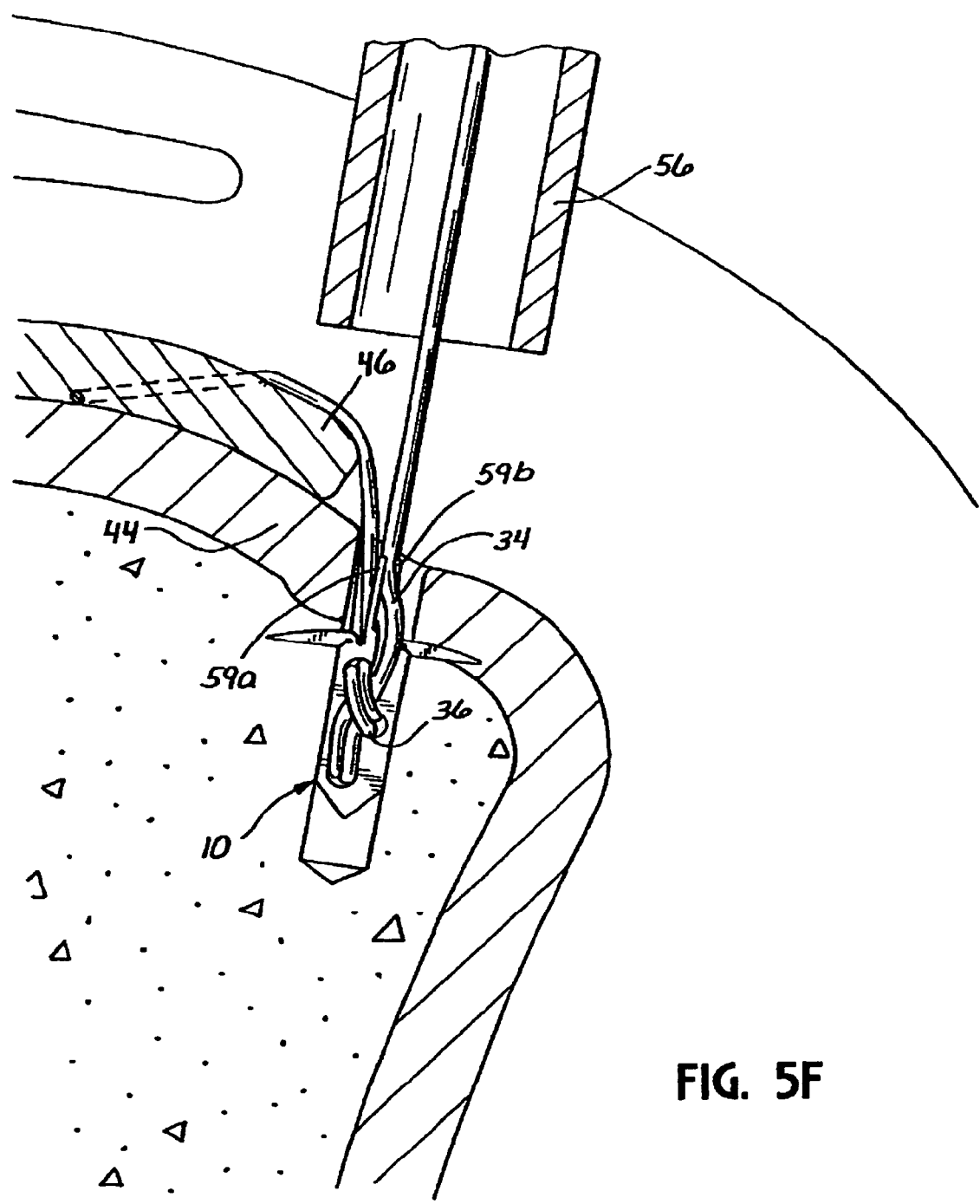
Figure 5G:
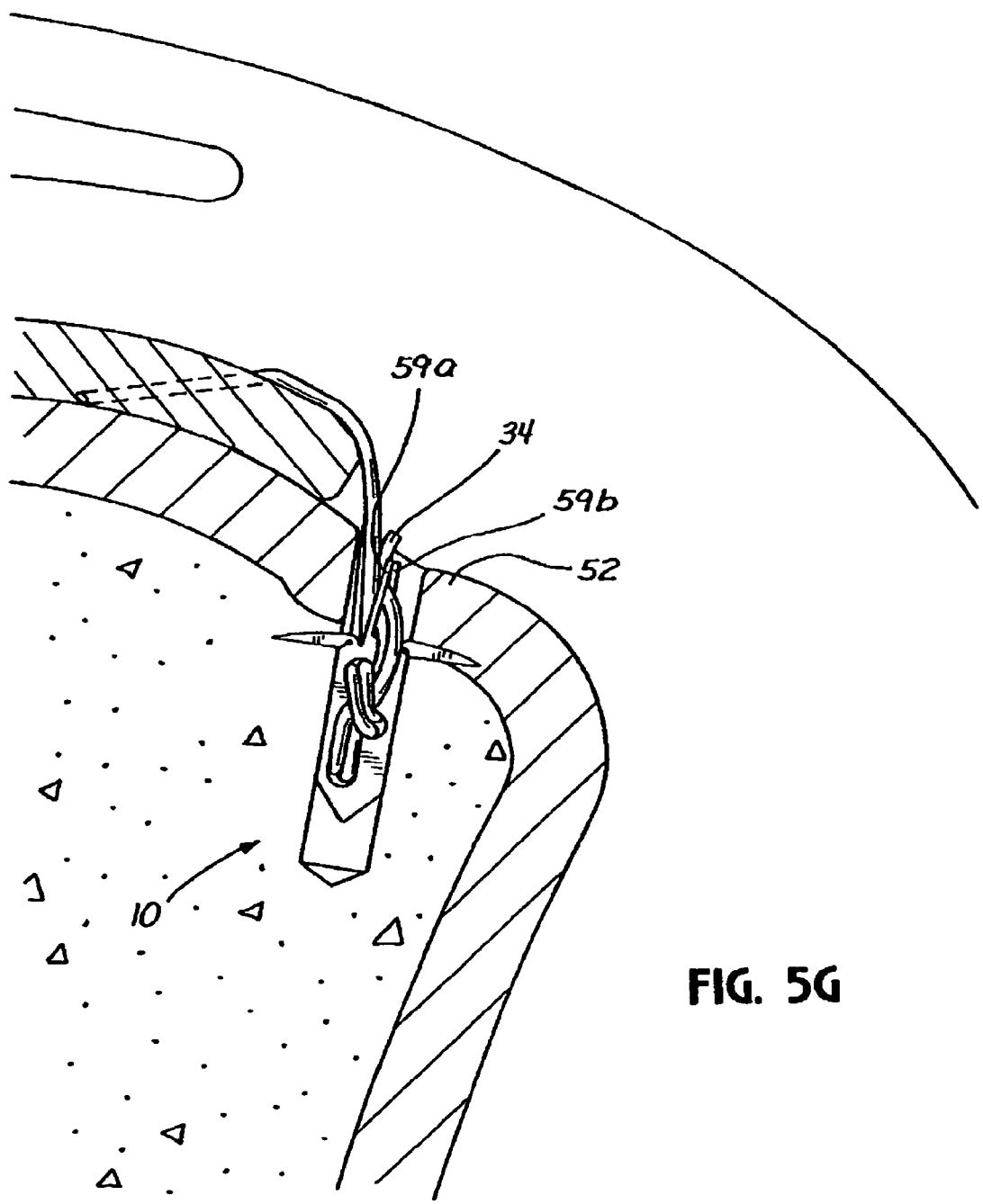

In FIG. 5f additional tension has been applied to the proximal end of the suture 34, and, in comparing the position of the rotator cuff 46 as illustrated in FIGS. 5e and 5f, it may be seen that the rotator cuff 46 has been pulled down against the cortical bone 52 by the manual action of creating tension on the loose legs of the suture 34. This tightening of the suture 34 and the subsequent approximation of the rotator cuff 46 to the bone 52 is made irreversible by the frictional force between the suture 34 passing through the suture loop 36. In order to absolutely assure that the suture 34 may not loosen, the suture 34 is then preferably threaded between two tabs 59a, 59b which have been formed at the proximal end of the bone anchor 10 as a result of the breaking of the weak links 22a,b. Then, as shown in FIG. 5g, the ends of the tabs 59a, 59b may be pinched together tightly against the suture 34 in order to secure the loose ends of the suture 34 to the proximal end of the bone anchor 10 and to prevent any potential loosening or unraveling of the suture 34. The suture 34 may then be cut, as illustrated in FIG. 5g, at the outer edge of the cortical bone 52 and the excess suture removed to complete the inventive procedure.

Figure 5H:
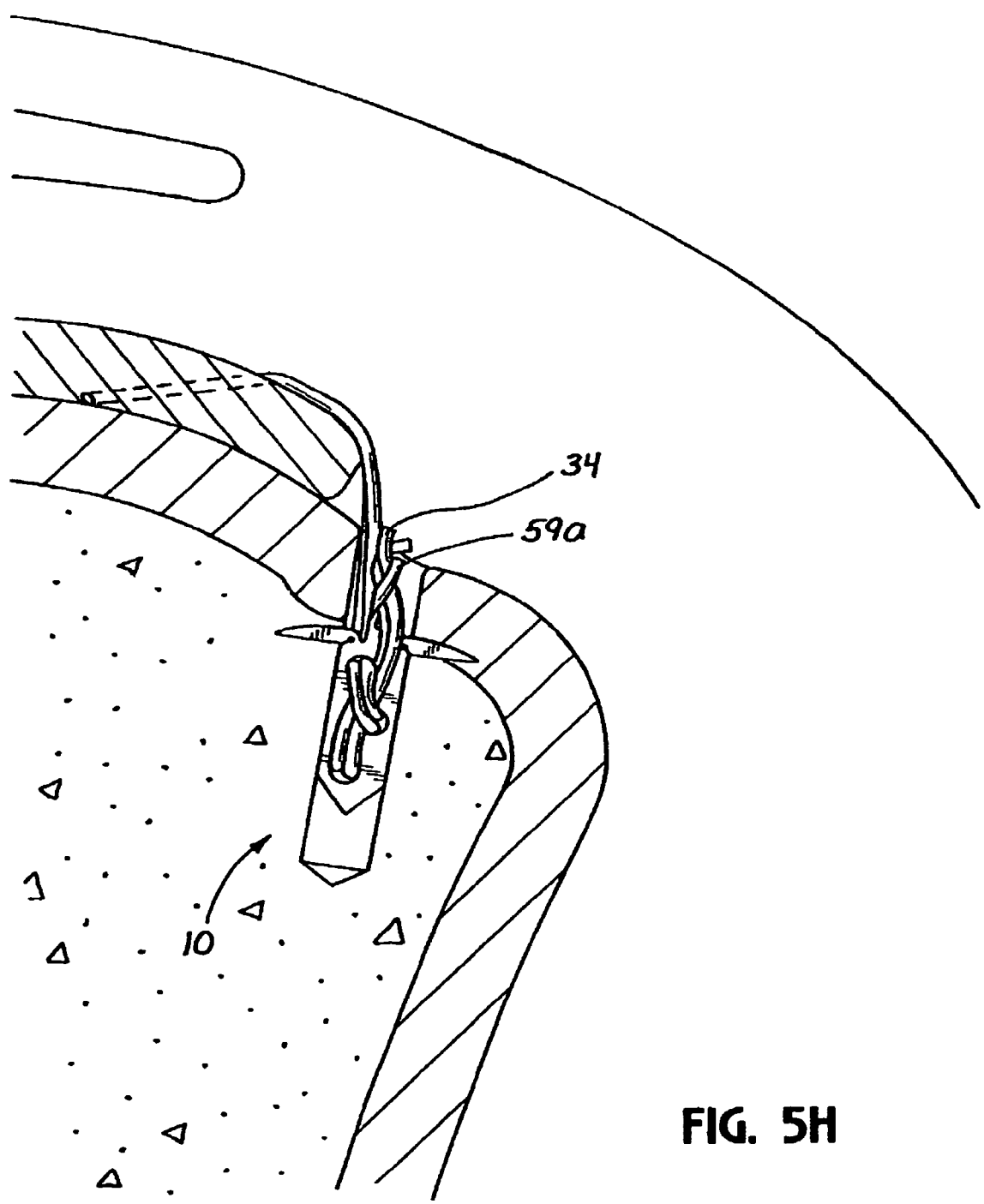
Figure 51:
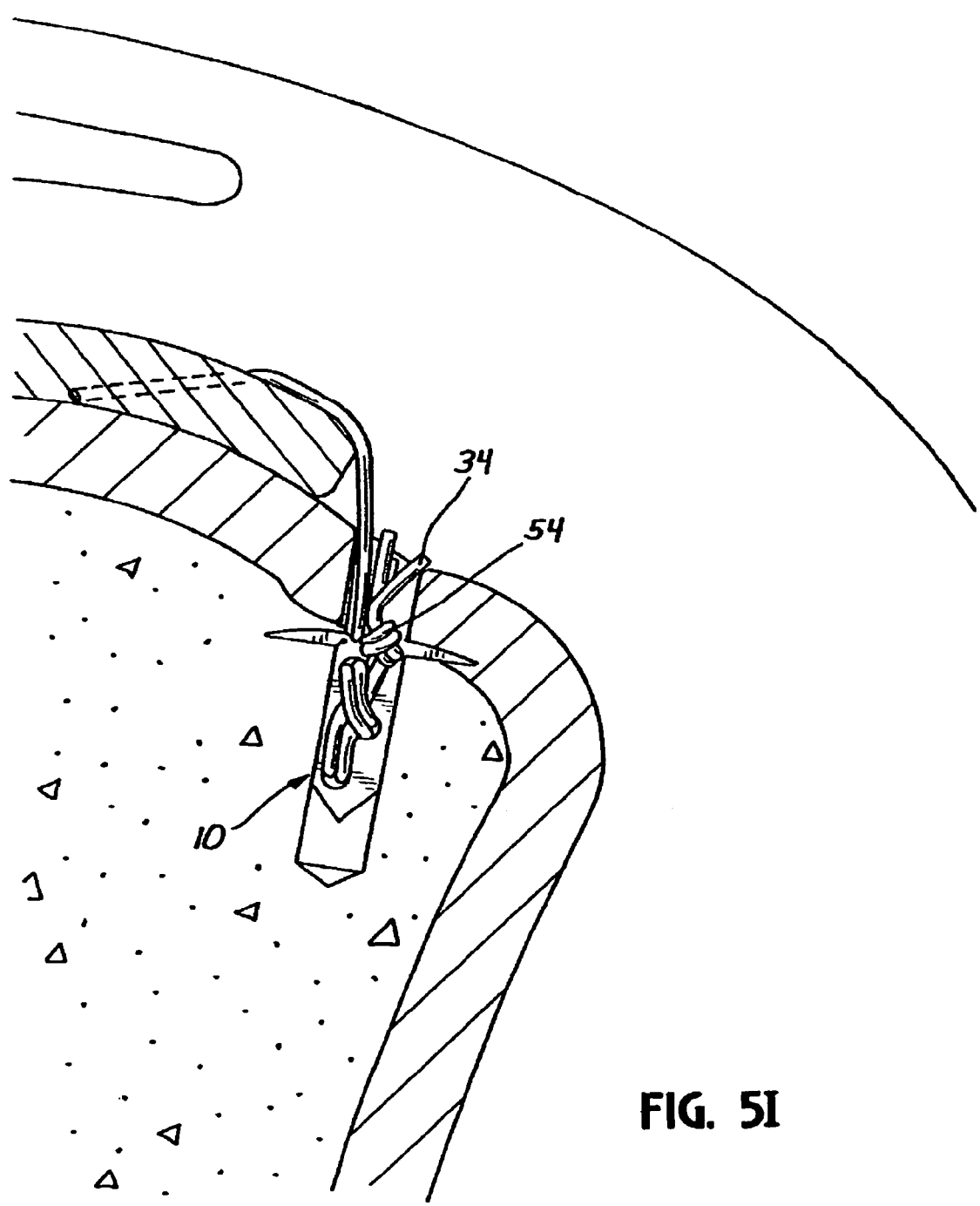
Figure 6:
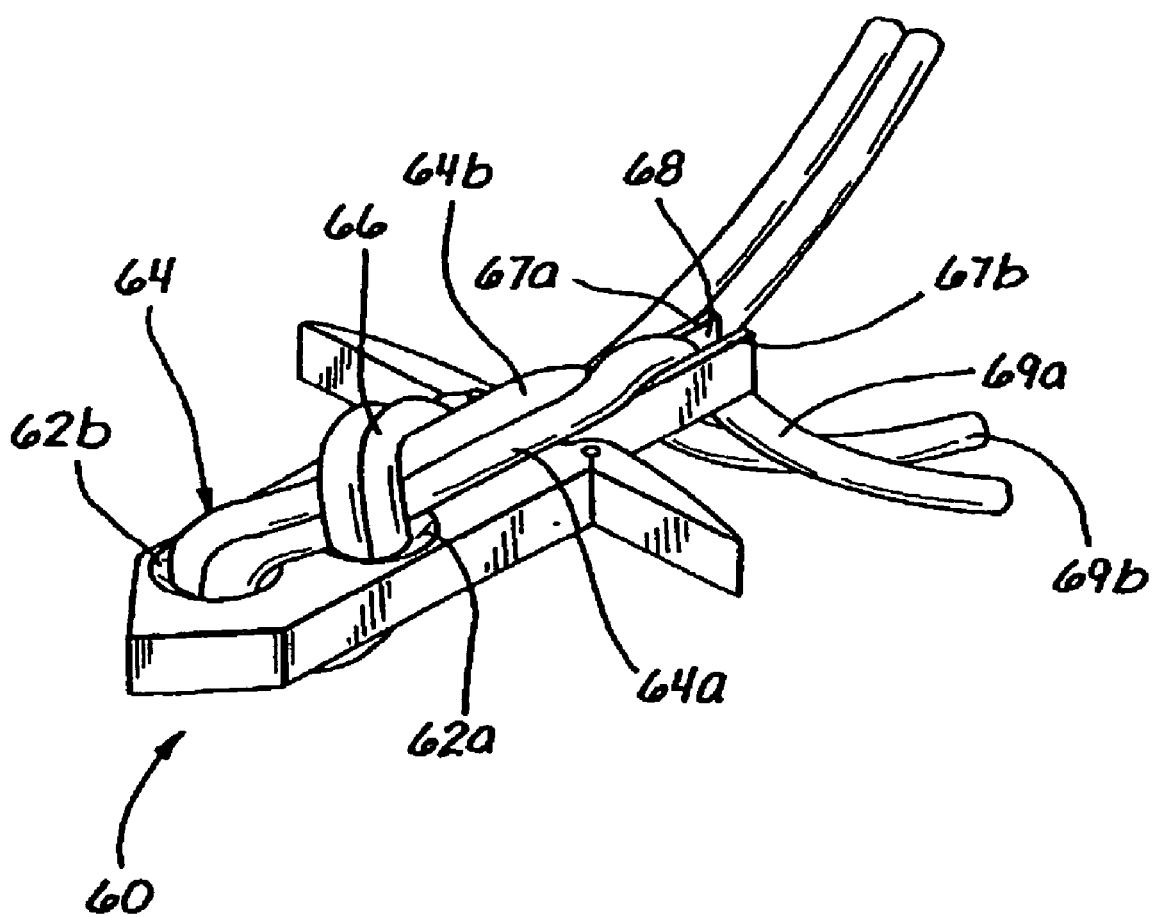
FIG. 6 is a perspective view of an inventive anchoring device of the type shown in FIGS. 1-5I, illustrating one alternative approach for locking the suture in place.

Alternative methods for preventing loosening or unraveling of the suture 34 from the bone anchor 10 are illustrated in FIG. 5h, wherein the tabs 59a, 59b are shown as having been twisted together around the loose ends of the suture 34 (as opposed to being merely pinched together, as shown in FIG. 5g), and in FIG. 5i, wherein a knot 54 is illustrated as having been tied in the suture at the proximal end of the bone anchor 10 (in which case the tabs 59a, 59b are not required). In FIG. 6, another alternative approach is illustrated, wherein an alternative bone anchor 60 has only two apertures 62a, 62b, as opposed to the three suture retaining apertures illustrated in connection with the earlier embodiments. In this embodiment, a length of suture 64 (which preferably comprises two free legs 64a, 64b) is threaded from the top side of the bone anchor 60 down through the eyelet hole 62a, then up through the eyelet hole 62b, and is passed under a loop 66 between the eyelet hole 62a and the body of the bone anchor 60. At the proximal end of the bone anchor 60 are two tabs 67a, 67b that define a slot 68. Free suture ends 69a, 69b are threaded into the slot 68, which by nature of the shape of the tabs 67 is tapered. As the suture ends 69a, 69b are pulled down into the slot 68 they are wedged and held by frictional force to prevent the sutures from loosening as discussed above.

Figure 7:
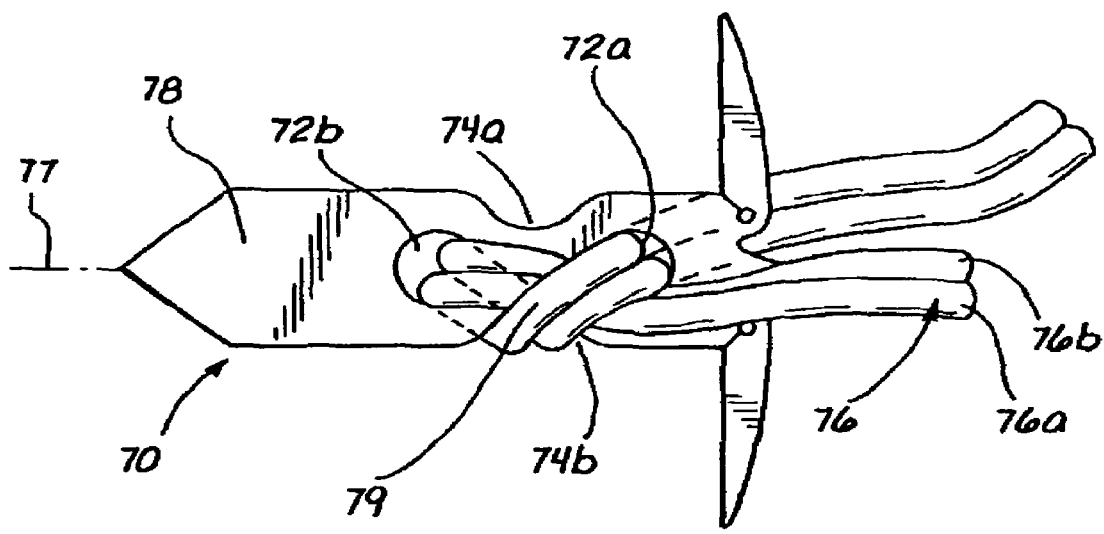
FIG. 7 is a plan view of an alternate embodiment of the inventive bone anchor device.
Figure 8:
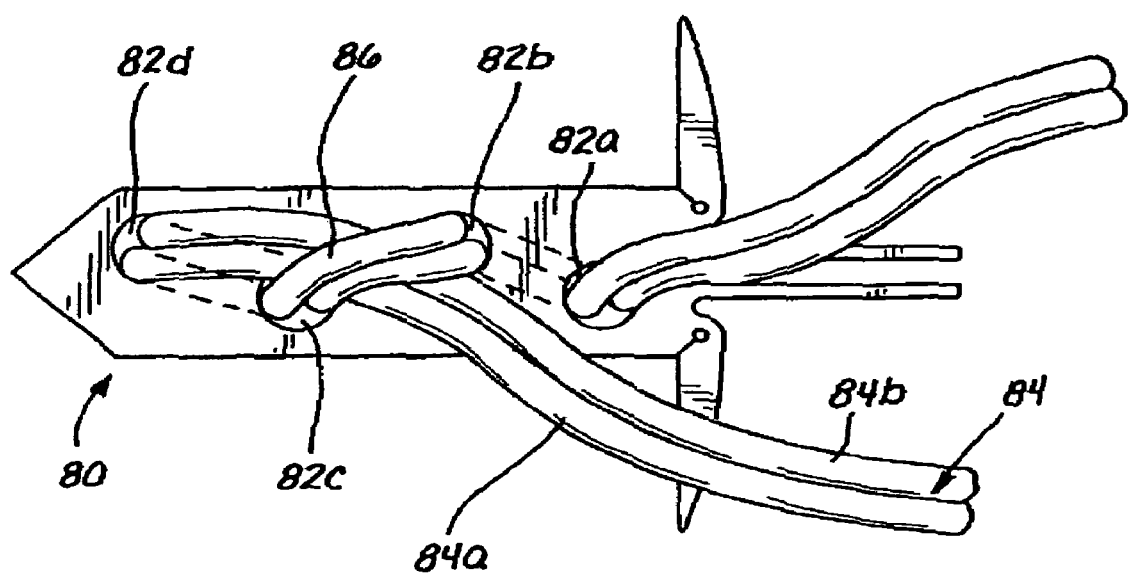
FIG. 8 is a plan view similar to that of FIG. 7, illustrating another alternate embodiment of the inventive device.

Additional alternative embodiments of the present invention may be seen by referring to FIGS. 7-8. FIG. 7 illustrates an alternative bone anchor 70 of the same general shape as that shown in prior embodiments, having two axially spaced eyelet holes 72a, 72b and with the addition of two troughs 74a, 74b forming a waist near the middle section of the bone anchor 70. It will be noted that in this waisted embodiment, the two eyelet holes (or suture retaining apertures) 72a, 72b are axially aligned, meaning that they are both centered on the longitudinal axis 77 of the anchor 70, as opposed to the prior illustrated embodiments, wherein the axially spaced apertures are offset from the longitudinal axis, in staggered fashion. This difference is possible because of the waisted configuration of the anchor body 78, which permits the wrapped suture lengths to achieve the same angled suture orientations as in the prior embodiments.

In this embodiment, a length of suture 76, comprising free legs 76a, 76b, is threaded from the rear side of the bone anchor 70 through the eyelet hole 72a, then weaved about the anchor body 78 through the trough 74b from the front side of the bone anchor 70 and back to the rear side of the anchor body 78. The suture 76 is then threaded through the eyelet hole 72b to the front side of the bone anchor 70 and passed through a loop 79 created between the eyelet hole 72a and the trough 74b. In all respects, the deployment of the bone anchor is essentially the same as with those anchors described above, and it should be clear that the tension in the suture 76 as it passes through the loop 78 creates a binding force similar to that previously described with the 3 hole anchor.

In FIG. 8, an alternative embodiment illustrated as a bone anchor 80 is virtually the same in shape, description and deployment to the preferred embodiment herein described with the exception that there are four eyelet holes 82a, 82b, 82c, and 82d instead of three such eyelet holes. The purpose for discussing this embodiment is to emphasize the general principle that, though three suture retaining apertures are preferred, any number of such apertures may be employed, if desired, within the scope of the present invention. In this figure, a length of suture 84, preferably comprising free legs 84a, 84b, as discussed supra, is threaded from front to rear through eyelet hole 82a, from rear to front through eyelet hole 82b, from front to rear again through eyelet hole 82c, and, finally, threaded from rear to front through eyelet hole 82d. It is then passed through the loop 86 created between eyelet holes 82b and 82c and tension applied as fully described in connection with the preferred embodiment, supra. Again, it is the tension in the suture 84 that creates the binding force in the loop 86.

It is to be understood that the figures of the bone and anchors seen above are purely illustrative in nature, and are not intended to perfectly reproduce the physiologic and anatomic nature of the humeral head as expected to be seen in the human species, nor to limit the application of the inventive embodiments to repair of the rotator cuff. The invention is applicable to many different types of procedures involving, in particular, the attachment of connective or soft tissue to bone.

Connective tissue such as ligaments, cartilage and tendons may tear and detach from the bone and muscle to cause pain and discomfort. One such tissue is the glenoid labrum in the shoulder, which, if torn from its associated bone, may cause pain and inability to elevate and rotate the arm. The torn tissue may result in complete separation of the tissue from the bone, but the tear may be partial, starting from a small lesion on the tissue.

A torn connective tissue can surgically be reattached to the bone and muscle by an open procedure that involves making an incision into the body, and suturing the tissue to the bone and muscle. In one such procedure, the tissue, if not already completely detached, is completely detached from the bone and the bone is debrided to match the edge of tissue at the tissue/bone reattachment location. The bone is also abraded and notched at the reattachment location to expedite healing. To reattach the tissue to the bone, a series of small diameter holes referred to as transosseous tunnels are punched through the bone over a distance of about 2 cm to 3 cm on the bone. One end of the is suture is attached to the tissue and at the other end of the suture is attached to the bone by threading the suture through the transosseous tunnels, and tying the suture on intact bone between two successive tunnels; thereafter, the incision is closed.

As will be appreciated, because the open procedure involves a large incision in the skin and the removal and subsequent reattachment of muscle to bony structures, the patient may experience postoperative discomfort and a relatively long recovery time.

In an alternative procedure that minimizes the incision and reduces postoperative discomfort, the reattachment is done arthroscopically. In an arthroscopic procedure the surgeon reconnects the tissue to the bone by working through a small trocar portal into the body. In one arthroscopic procedure, rather than using transosseous tunnels to thread the suture through the bone, which is difficult to achieve arthroscopically, the disconnected tissue is connected to the bone by attaching the tissue to one end of a suture, securing the other end of the suture in a bone anchor, and embedding the anchor in the bone.

Although arthroscopic procedures are less invasive than open procedures, it is not always the procedure used. One reason is that arthroscopic suturing requires a high level of skill not possessed by all surgeons. Another is that arthroscopic suturing is clumsy and time consuming and only the simplest stitch patterns can be utilized. Further, with arthroscopic suturing it is difficult to judge the proper tightness of the suture knot, or the tension on the suture, or easily adjust the suturing. Further, with arthroscopic suturing, the knots on the suture may end up on top of the tissue as a knot bundle which, postoperatively, can be problematic if it causes irritation when the tissue is exercised.

In reattaching the tissue to the bone, besides the problems arising from using the suture, other problems may arise due to the anchor. For example, with anchors that use an eyelet to attach the suture to the anchor, because the eyelets are small with a tight radius as in the eye of a needle, the pressure on the suture in the eyelet is high which may cause the suture to fail at the eyelet when the anchor is embedded and the tissue is tensioned.

Another problem with anchors is that due to the need to minimize the profile of the anchor projecting above the bone, an attachment structure such as a screw is used to attach the anchor to the bone; however, a problem with the attachment structures is their tendency to loosen and detach the anchor. Besides, these attachment structures also project an undesired profile on the bone surface.

An embeddable anchor that does not project a profile on the bone is disclosed in commonly assigned and co-pending U.S. patent application Ser. No. 11/143,132 filed on Jun. 1, 2005, herein incorporated by reference for all purposes. In various embodiments the anchor utilizes the difference in hardness in the bone between the outer, tough cortical layer, and the inner, airy vascular cancellous layer, for embedding the anchor in the bone. To utilize this difference in the bone, the anchor is designed with a longitudinal axis having a proximal longer portion and a distal shorter portion, and a mechanism to rotate the portions relative to each other. The anchor is also designed to be pre-threaded with suture.

To use this anchor, a hole is drilled through the cortical layer of the bone into the cancellous layer to receive the anchor. The anchor is deployed in the hole past the cortical layer. Thereafter, the longer axial portion is rotated orthogonally relative to the shorter axial portion such that the longer portion is seated against the underside of the cortical layer in the hole, thereby embedding the anchor in the bone.

Another embeddable anchor that does not rely on an attachment structure is an anchor that uses a pop-rivet structure to embed the anchor. This type of anchor requires forming a hole in the cortical bone into which a split shaft is inserted. The split shaft is hollow and comprises a tapered plug leading into an inner lumen. To use the anchor, the tapered plug is retracted out through the top of the shaft; the anchor is inserted into a hole in the bone; and the plug is inserted into the inner lumen to flare the tapered portion of the split shaft outwardly, thereby embedding the anchor in the bone.

U.S. Pat. No. 5,324,308 to Pierce ("Pierce") discloses an anchor wherein a distal wedge component comprising two holes at its base is used to thread a suture. When the assembly is placed in a hole in the bone and the suture is tensioned, the distal wedge rides up against a proximal wedge block, expanding the projected area within the drilled hole, to embed the anchor in the bone.

U.S. Pat. No. 5,383,905 to Golds et al ("Golds") discloses an anchor wherein a bead member having a longitudinal bore and an anchor member adapted to be slidably inserted within the bore of the bead member is used to secure the suture. The anchor member includes two axial compressible sections that define a passageway to receive two end portions of a suture loop. The axial sections collapse radially inwardly upon insertion of the anchor member within the bore of the bead member to wedge the suture within the passageway.

U.S. Pat. No. 5,584,835 to Greenfield ("Greenfield") discloses an anchor comprising a pug to secure the suture and embed the anchor in the bone. In Greenfied, an anchor portion is adapted to accept the plug and the suture, and the plug is configured such that when it is forced into its receptacle in the anchor, the suture is held by friction between the wall of the anchor and the body of the plug.

U.S. Pat. No. 5,702,397 to Goble et al ("Goble") discloses an anchor comprising a threaded body with an inner cavity to anchor the suture. The cavity is open at one end of the threaded body, and joins two lumens that run out to the other end of the threaded body. Within the cavity is disposed a gear, journaled on an axle. A length of suture is threaded through one lumen, around the gear, and out through the other lumen. A ball is disposed within the cavity to ride against a tapered race and lock the suture in place.

U.S. Pat. No. 6,652,561 to Tran ("Tran"), hereby incorporated herein by reference for all purposes, discloses an embeddable anchor that does not require tying a knot on the suture to secure the tissue, and which allows for adjusting the tension on the suture after the tissue is attached to the anchor. In one embodiment, the anchor comprises an anchor body, a plurality of suture retaining holes disposed in the anchor body, and a deployable structure for embedding the anchor in the bone. In various embodiments the suture is attached to the tissue and the ends of the suture are threaded through the anchor such that on pulling on the suture, the suture is locked on the anchor, thereby attaching the tissue to the anchor.

In procedures for reattaching body tissue to bone, there is a continuing need for embeddable anchors that eliminate the need to tie a suture knot on the tissue, and simplify the procedure. It is therefore and objective to address these needs.

As used herein the portion of the suture fixed or attached to tissue or bone is referred to as the "standing end"; the other end of the suture that extends towards the handler, or is manipulated by the handler, is referred to as the "working end" or tail of the suture. The distal end of the implant or suture is that portion of the suture located away from the handler; and the proximal end is located next to or near the handler.

Figure 9:
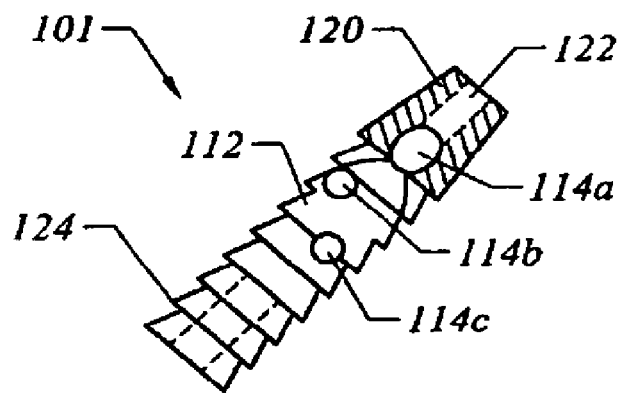
FIG. 9 is an illustration of the suture lock and bone anchor in one embodiment.
Figure 11:
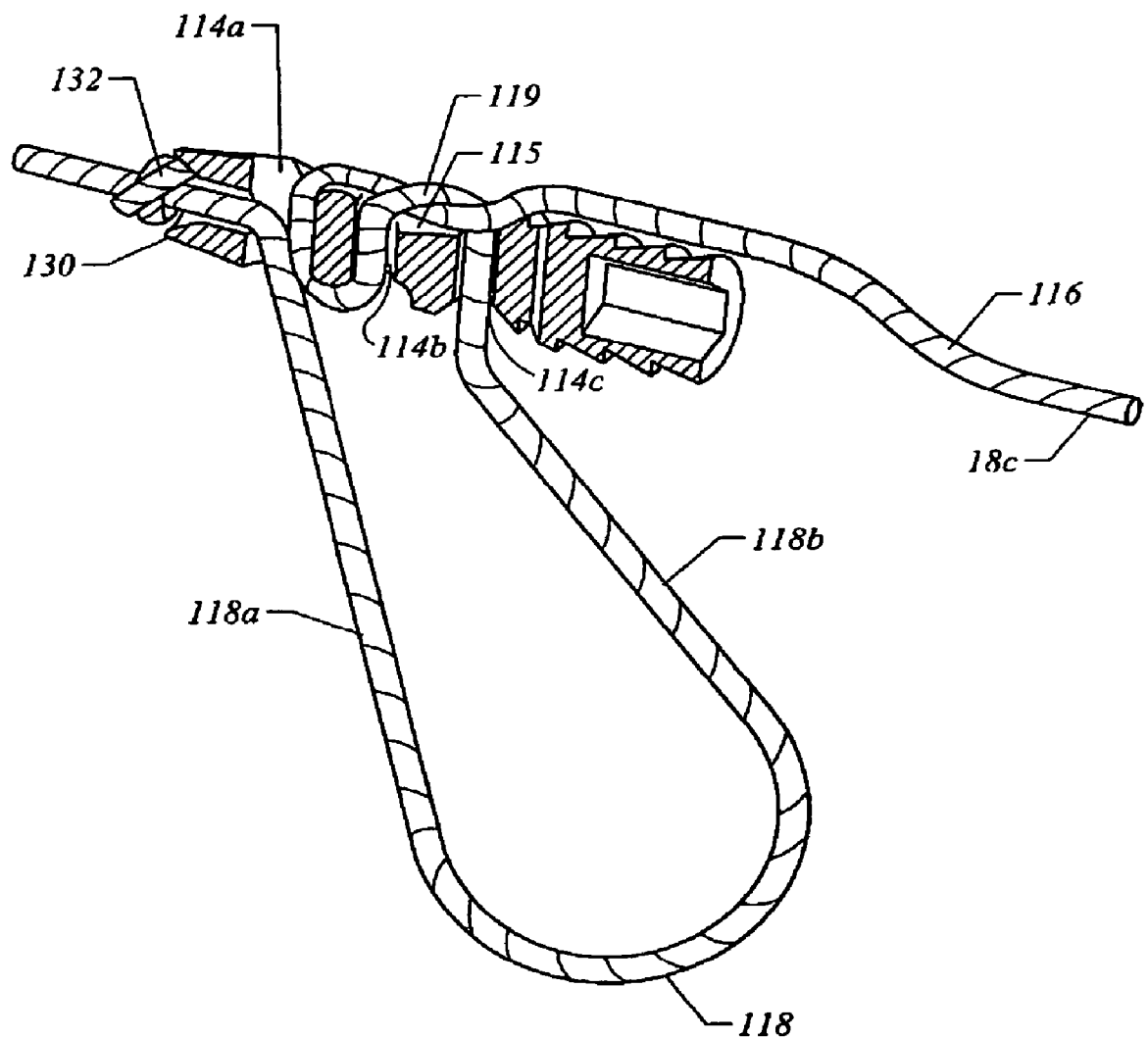
FIG. 11 is an illustration of a cross section of the suture lock and bone anchor with a single-tailed suture in one embodiment.
Figure 12:
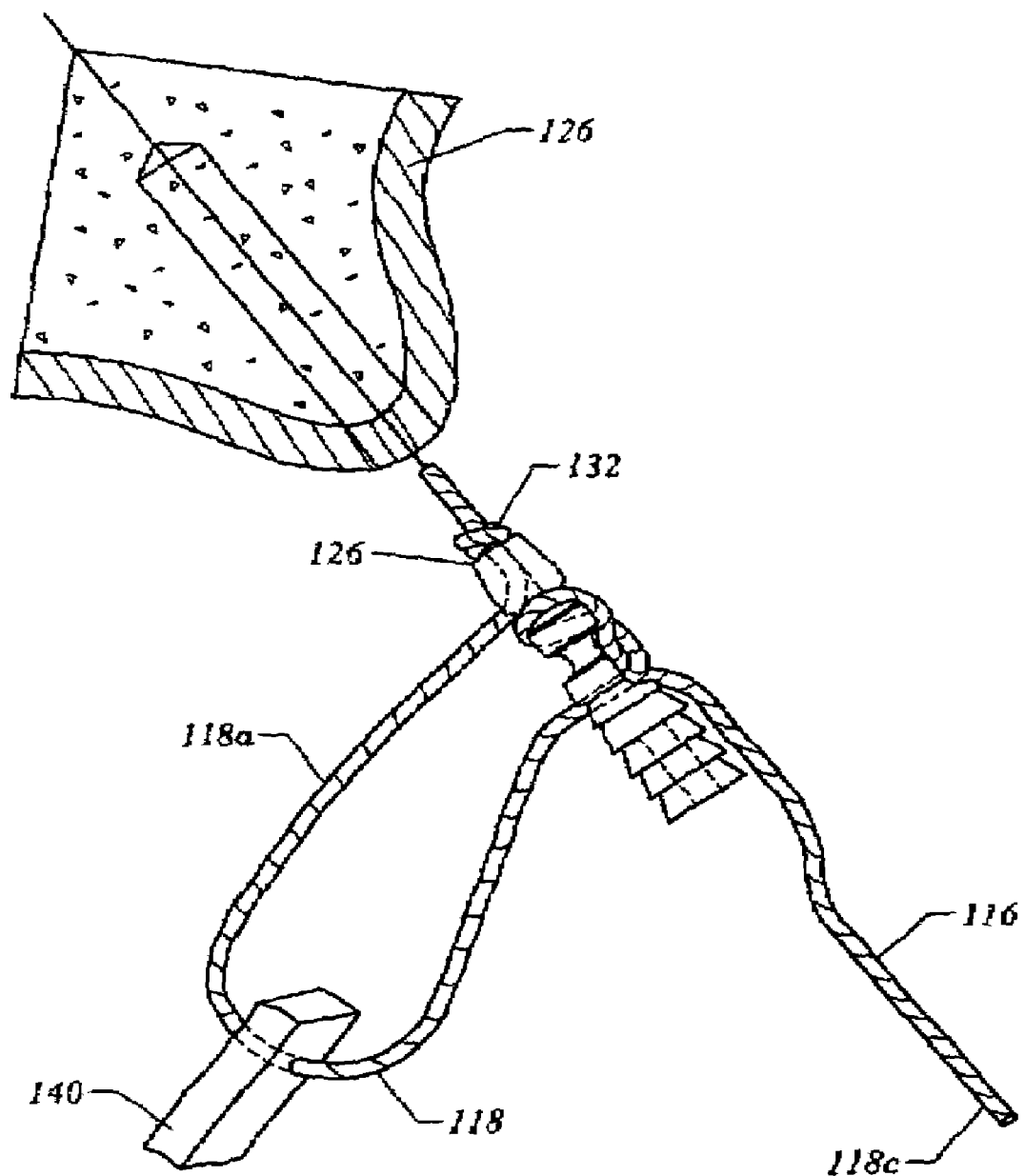
FIG. 12 is an illustration of the suture lock and bone anchor cinching a tissue on a suture loop in one embodiment.
Figure 13:
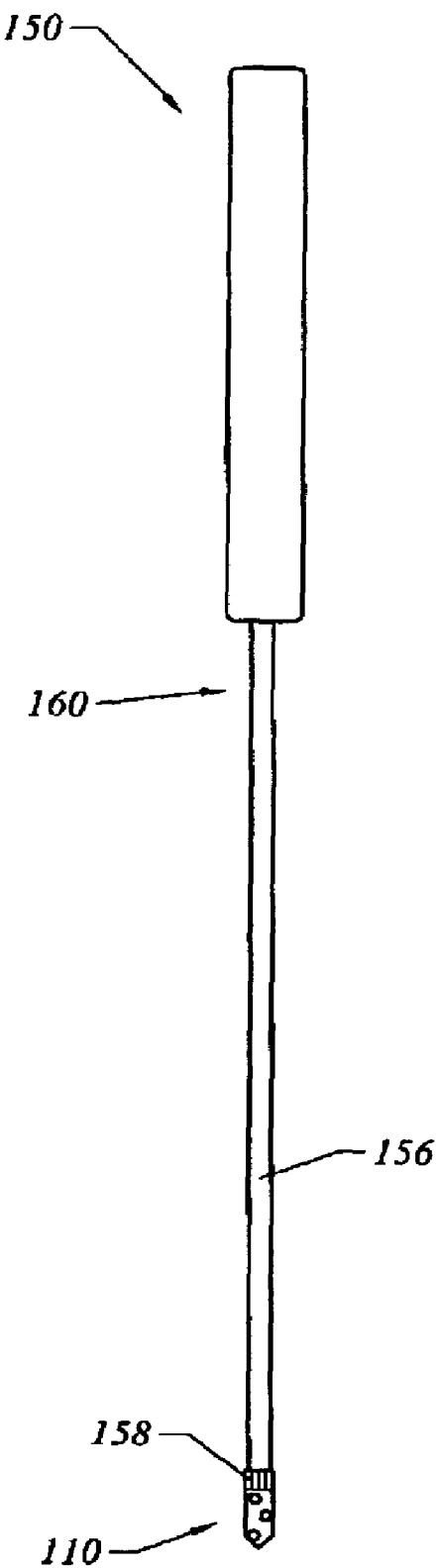
FIG. 13 is an illustration of a deployment system for embedding the suture lock and bone anchor in a bone in one embodiment.
Figure 14:
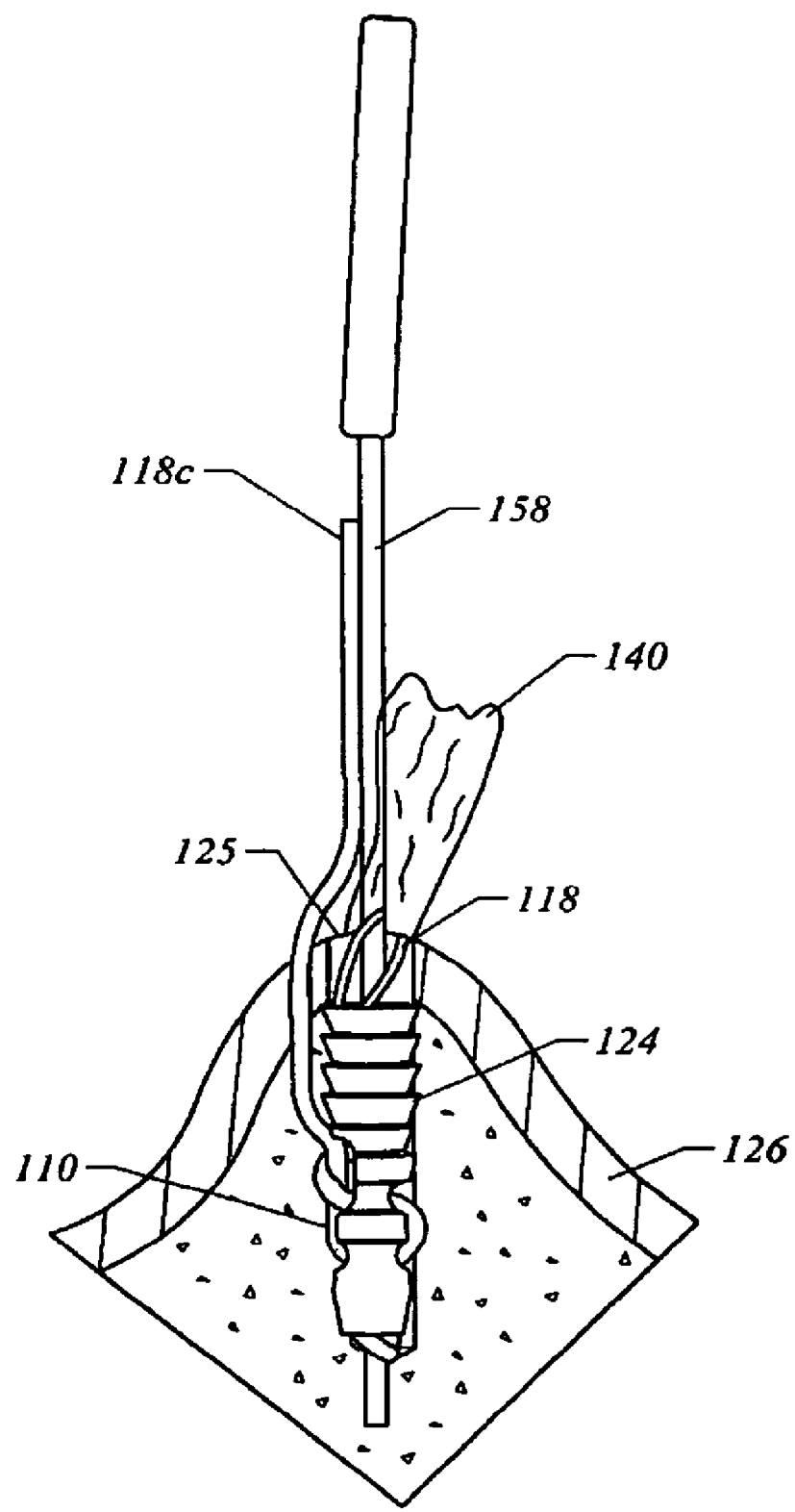
FIG. 14 is an illustration of the suture lock and bone anchor embedding tissue in a bone in one embodiment.
Figure 15:
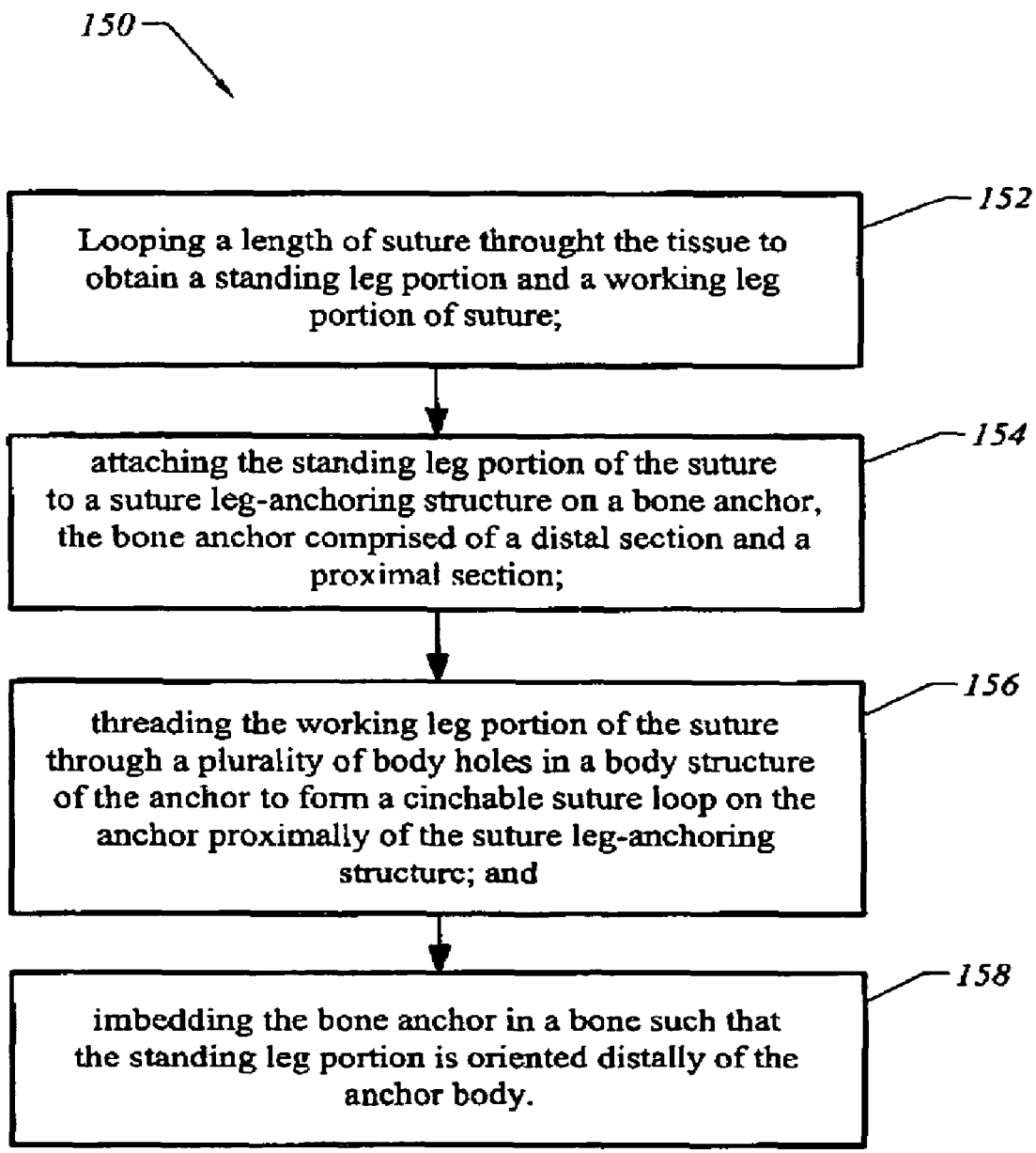
FIG. 15 is a method of anchoring connective tissue to bone using the suture lock and bone anchor in one embodiment.

The present suture lock and bone anchor in one embodiment, without a suture, is illustrated in FIG. 9; the present anchor in one embodiment with a suture is illustrated in FIGS. 10, 11, 12, and 14; and the anchor attached to a deployment device for inserting the anchor in a bone is illustrated in FIGS. 13 and 14. A method of anchoring tissue in the bone with the present anchor is illustrated in FIG. 15.

With reference to FIGS. 9-12, the anchor (101) comprises: a body structure (112) having a plurality of body holes (114a, 114b, 114c) adapted to thread the suture (116, 118, 132) through the anchor and cinch a portion of the suture (119) on the body structure (112) such that a fixed loop (118) is formed on the suture between the standing leg portion (118a) and the working leg portion (118b) of the suture; a suture leg-anchoring structure (120) adapted to fasten the standing leg portion of the suture (118a) onto the anchor; and a bone embedding structure (124) adapted to embed the anchor in the bone (126) and resist pullout.

Figure 10:
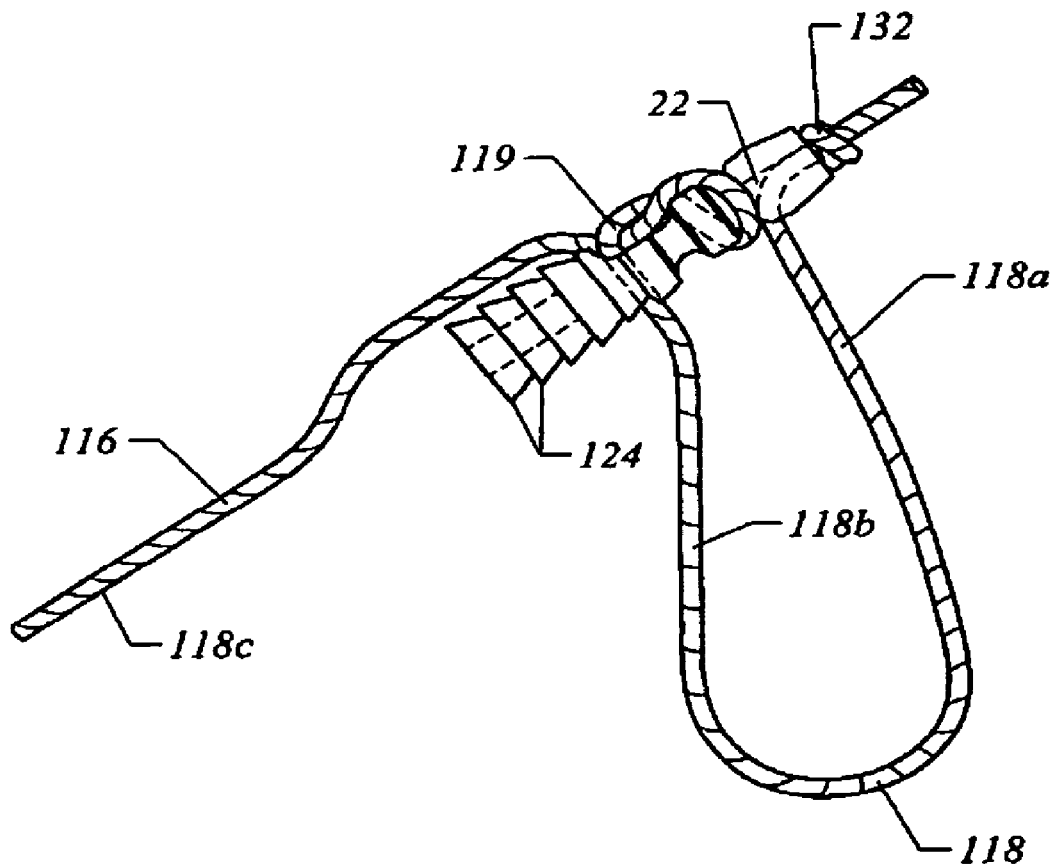
FIG. 10 is an illustration of the suture lock and bone anchor with a single-tailed suture in one embodiment.

With reference to FIGS. 9-12, the body structure (112) comprises body holes (114a, 114b, 114c) that extend through the body structure. The body holes are adapted for threading the suture (116, 138, 132) through the body structure and are disposed proximally of the suture leg-anchoring structure (120). In one embodiment the body holes are offset from each other relative to a longitudinal axis of the body structure to facilitate cinching the suture at a the cinch point (119) in the proximity of the body holes on the body structure. As is illustrated in FIG. 9-11, a surface on the body structure is flattened (115) under the cinch point (119) to better seat the cinched suture on the body structure. The diameter of the body holes is sized to thread at least one diameter of suture (116), and one of the body holes (114a) as is illustrated in FIG. 11 is sized to pass at least two diameters of the suture.

With reference to FIGS. 10-12, the suture leg-anchoring structure (120) is adapted to fasten a standing leg portion of the suture (118a) such that the tissue (140) can be cinched to the body structure (112) by looping a section of the suture (118) through the tissue (140), fastening the standing leg portion (118a) of the loop (138) onto the suture leg-anchoring structure (120), threading the suture (116, 118, 132) through the body holes (114a, 114b, 114c), and pulling on the working end or tail portion (118c) of the suture (116) to tighten a cinched portion of the suture (119) on the body structure (112). The standing leg portion of the loop (118a) is fastened in the suture leg-anchoring structure (120) by threading the working leg (118c) distally through the suture leg-anchoring hole (122), and tying a suture-retaining knot (132) on the suture outside of the hole (122). To ensure that the suture is securely attached to the suture leg-anchoring structure (120), the cross-section of the suture-retaining knot (132) is made larger than the cross-section of the suture-anchoring hole (122). In an alternative embodiment not shown in the figures, the standing leg of the loop (118a) is fastened in the suture leg-anchoring structure (120) by threading the standing leg portion (118a) distally through the suture-anchoring hole (122), and tying the suture on a structure disposed outside of the sure anchoring hole (122).

As is illustrated in FIGS. 1-4, the suture leg-anchoring structure (120) is disposed distally of the body structure (112) and comprises a suture leg-anchoring hole (122) adapted to fasten the standing suture leg (118c) on the shoulder surface (130) of the suture-affixing hole (122). The suture-affixing hole (122) is connected to the first body hole (114a) in the body structure (112) through the suture leg anchoring structure (120). In one embodiment the shoulder surface (130) comprises a hook structure and a bar structure for attaching the standing leg of the suture (118a) on the suture leg-anchoring structure (120).

With reference to FIGS. 1-3 the bone-embedding structure (120) is attached on the body structure (112) proximal to the suture leg-anchoring structure (120). The bone-embedding structure (120) comprises a plurality of barbed structures (124) oriented towards the distal end of the anchor to embed the anchor in the bone. As is illustrated in FIG. 14, the barbed structures (124) taper towards the distal end of the anchor to resist proximal pullout of the anchor from the bone (126). In one embodiment the bone-imbedding structure (124) adapted to resist pullout when subjected to up to about sixteen pounds load on the suture loop (118).

In various embodiments, the anchor (110) including body structure, the suture leg-anchoring structure (120) and the bone-embedding structure (124) are comprised of an implantable material selected from the group consisting of a metal, a polymer, a ceramic or combinations thereof. Such materials are known to one ordinarily skilled in the art and are generally available.

With reference to FIGS. 10-12 the suture (118) attached to the body tissue (140) is threadable through the anchor (110) to form a loop (118) and a cinch point (119) on the suture on the body structure (112), to cinch the tissue and suture to the body structure (112) by looping the suture through the tissue (140) to form the suture loop (118); threading the standing leg (118a) of the suture loop through the suture leg-anchoring hole (122) in the suture leg-anchoring structure (120); tying a suture retaining knot (132) on the distal end of the standing leg (118a) of the suture loop projecting out of the suture anchoring hole (122), such that the suture retaining knot(132) is held outside of the suture leg-anchoring structure, on the shoulder (130) of the leg-anchoring structure (120); and threading the working leg (118b) the suture loop (118) through the body holes (114a, 114b, 114c) in the body structure (112) to form the cinch point on the suture (119) on the body structure (112). Consequently, on pulling on the tail (118c) of the working end of the suture (116), the retaining suture knot (132) holds the distal end of the suture on the shoulder (130) of the suture leg-anchoring structure (120), tightens the suture retaining knot (132) on the suture anchoring hole (128), and tighten the cinch point (119) of the tissue on the body structure (112), to fix the size of the loop (118), and cinch the loop and tissue to the body structure (112).

With reference to FIG. 3, the cinch point (119) of the suture on the body structure (112) is formed by anchoring the standing leg (118a) of the loop (118) in the suture leg-anchoring structure (120) as described above; threading the suture through the third body hole (114c), then through the second body hole (114b), then through first body hole (114a), an then through the space under the suture between the second and third body holes. Pulling on the tail or working end portion of the suture (118c) suture tightens the suture on the body structure. A suture loader apparatus that automatically threads the suture on the anchor is this manner is described in co-pending U.S. patent application Ser. No. 11/365,266, herein incorporated by reference for all purposes.

An anchor deployment device (150) that can be used to insert the anchor (110) in a bone is illustrated in FIG. 13. In one embodiment the anchor deployment device comprises a suture reel through which the working end (118c) end of the suture is tensioned to fix the size of the loop (118) and tension the suture on the body portion (112) to form cinch point (119) as is illustrated for example in suture loader apparatus described in co-pending U.S. patent application Ser. No. 11/365,266, supra.

With reference to FIG. 14, in one embodiment the present single-tailed suture lock and bone comprises is system for embedding the anchor and tissue to the bone (126) using the present anchor (110), wherein a first (114a), a second (114b), and a third body hole (114c) in a body structure (112) are adapted for threading a suture (116, 118a, 118b, 132) through the anchor; a suture leg-anchoring structure (120) disposed distally of the body structure; and the suture having a standing leg (118a) and a free leg (118b), wherein the free leg is attachable to the suture leg-anchoring structure, and the suture is configurable into a cinch point (119) through the body holes, for cinching the suture and hence the tissue on to the body structure by pulling on a tail portion or working end portion (116c) of the suture, as described above. The bone anchor (10) is inserted in the bone through a trocar (158) by means of the barrel (156) of the deployment device (150), into the hole (125) in the bone (126). The free leg (118c) of the suture is drawn tight against the bone anchor (110) by pulling on the tail (118c) proximally out of the hole as the anchor is inserted in the bone (126). As is illustrated in FIG. 14, the barbs (124) on the bone anchor (110) enhances embedding the anchor (110) in the bone, and resist pullout of the anchor form the bone. After the anchor is embedded, the deployment device (150) is removed from the trocar (158) by withdrawing it proximally through such trocar.

With further reference to FIG. 14, additional tension can be applied to the suture by pulling on the loose leg of the suture (116). This tightening of the suture (116, 118a, 118b, 132) and the subsequent approximation of the tissue to the bone resist pullout of the tissue passing through the suture loop (138). The suture (116) may then be cut outside of the cortical bone (126) to complete the procedure.

With reference to FIG. 15, in one embodiment the present suture lock and bone anchor is useable for attaching tissue to bone by a method comprising the steps of (152) looping a strand of suture (116, 118a, 118b, 132) through the tissue (140) to obtain a loop comprised of a standing leg (118a) and a tail of suture (118c) as described above to attach the standing leg to the suture leg-anchoring structure (120) on a bone anchor (110). Thereafter, the suture is threaded through the plurality of holes (114a, 114b, 114c) in the body structure (112) of the anchor to form a knot (119) and a cinchable loop (118) proximally of the suture leg-anchoring structure (120). This can be done outside of the body of the patient. Thereafter the anchor with the suture loaded is attached to the anchor deployment device (150) and forwarded through a trocar to a hole drilled into the bone to receive the anchor. Any slack in the suture is taken up by pulling on the tail (118c) of the free end of the suture (116). By further pulling on the free-end of the suture the tissue is cinched closer to the anchor, to set the appropriate length of the suture loop. Close approximation of the tissue to the bone is achieved when the anchor is pounded into the hole in the bone. As will be appreciated by one ordinarily skilled in the art, the suture is secured to the anchor die to the dynamics of the knot. The pinching of the suture between the surface of the hole in the bone and the barbs on the proximal end of the anchor provides additional suture locking.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention. In particular, it is noted that the procedures, while oriented toward the arthroscopic repair of the rotator cuff and the labrum, are applicable to the repair of any body location wherein it is desired to attach or reattach soft tissue to bone, particularly using an arthroscopic procedure. Also, the various aspects of the invention described herein may be modified and/or used in combination with such other aspects also described to be part of the invention or disclosed in references discussed to form other advantageous variations considered to be part of the invention covered.

The invention claimed is:

1. A suture lock and bone anchoring system, comprising:
   an embeddable anchor body structure comprising a plurality of body holes adapted for threading a suture therethrough;
   a suture leg-anchoring structure disposed distally of the body structure; and
   a suture having a standing leg portion and a working leg portion threaded through the body holes,
   wherein the standing leg portion of the suture is attached to the suture leg-anchoring structure, and, wherein the body holes are disposed such that the working leg portion threads through a third body hole, a second body hole, a first body hole and a through a space under the suture between the second and third body holes so as to cinch the working leg portion between the suture and a flattened surface on the body structure.

2. The bone anchoring system of claim 1, wherein pulling on the suture working leg portion tightens the suture on the body structure.

3. The bone anchoring system of claim 1, where the suture is selected from the group consisting of a braded suture and a monofilament suture.

4. The bone anchoring system of claim 1, wherein the standing leg portion comprises a single strand of suture.

5. The bone anchoring system of claim 1, wherein the body structure comprises a plurality of barbed structures adapted for embedding the anchor in the bone.

6. A suture lock and bone anchoring system for attaching tissue to a bone, comprising:
   an embeddable body structure comprising a plurality of body holes;
   a bone-embedding structure adapted for retaining the body structure in a bone; and
   a length of suture loop threaded through the body holes,
   wherein the body holes are disposed such that the suture loop threads through a third body hole, a second body hole, a first body hole and a through a space under the suture between the second and third body holes, so as to cinch the suture between the suture and a flattened surface on the body structure.

7. The bone anchoring system of claim 6, wherein the bone-embedding structure is disposed proximally of the body structure.

8. The bone anchoring system of claim 6, wherein the suture leg-anchoring structure comprises a suture leg-anchoring hole adapted to fasten the standing leg.

9. The bone anchoring system of claim 6, wherein the suture leg-anchoring hole defines a shoulder for fastening the standing leg portion of the suture.

10. The bone anchoring system of claim 6, wherein the shoulder comprises a flat surface, a hook and a bar structure for fastening the standing leg.

11. The bone anchoring system of claim 6, wherein the shoulder is sized to prevent a knot on the standing leg from passing through the suture leg-anchoring hole.

12. The bone anchoring system of claim 6, wherein the body structure comprises a first body hole, a second body hole and a third body hole.

13. The bone anchoring system of claim 6, wherein the bone-embedding structure comprises a plurality of barbed structures disposed on the body structure.

14. The bone anchoring system of claim 6, wherein the body structure comprises a biocompatible material selected from the group consisting of a metal, a polymer, a ceramic or combinations thereof.

15. The bone anchoring system of claim 6, wherein the standing leg portion comprises a single strand of suture.

16. A method of anchoring tissue to bone, comprising:
   passing a length of suture through the tissue to obtain a standing leg portion and a working leg portion of suture;
   attaching the standing leg portion of the suture to a suture leg-anchoring structure on a bone anchor, the bone anchor comprised of a distal section and a proximal section;

threading the working leg portion of the suture through a plurality of body holes in a body structure of the anchor to form a cinchable suture loop on the anchor proximally of the suture leg-anchoring structure, wherein the cinchable loop is formed by anchoring the standing leg portion in the suture leg-anchoring structure, and threading the working leg portion through a third body hole, a second body hole, a first body hole and a space under the suture between the second and third body holes, whereby pulling on the working leg portion tightens the suture on the body structure; and embedding the bone anchor in a bone such that the standing leg portion is oriented distally of the anchor body.

17. The method of claim 16, wherein the standing leg portion comprises a single strand of suture.

18. The method of claim 16, wherein attaching the standing suture leg to the suture leg-anchoring structure comprises forming a knot on the standing leg portion, and threading the working leg portion of the suture through a plurality of body holes in the suture leg-anchoring structure, whereby on pulling on the working leg portion, the suture tightens on the anchor.

19. The method of claim 16, wherein the tissue comprises tissue of the labrum.

* * * * *